(12) United States Patent
Nilsson

(10) Patent No.: US 9,645,565 B2
(45) Date of Patent: May 9, 2017

(54) METHOD AND SYSTEM FOR DETERMINATION OF AT LEAST ONE PROPERTY OF A JOINT

(71) Applicant: COGNIBOTICS AB, Lund (SE)

(72) Inventor: Klas Nilsson, Lund (SE)

(73) Assignee: COGNIBOTICS AB, Lund (SE)

( * ) Notice: Subject to any disclaimer, the term of this patent is extended or adjusted under 35 U.S.C. 154(b) by 38 days.

(21) Appl. No.: 14/436,233

(22) PCT Filed: Oct. 21, 2013

(86) PCT No.: PCT/SE2013/051224
§ 371 (c)(1),
(2) Date: Apr. 16, 2015

(87) PCT Pub. No.: WO2014/065744
PCT Pub. Date: May 1, 2014

(65) Prior Publication Data
US 2015/0248121 A1    Sep. 3, 2015

(30) Foreign Application Priority Data
Oct. 23, 2012  (SE) ...................................... 1251196

(51) Int. Cl.
*G05B 19/18*    (2006.01)
*A61B 7/00*    (2006.01)
(Continued)

(52) U.S. Cl.
CPC ........ *G05B 19/0428* (2013.01); *B25J 9/1641* (2013.01); *H02P 29/00* (2013.01);
(Continued)

(58) Field of Classification Search
CPC ...... G05B 19/0428; G05B 2219/41059; G05B 2219/40381; B25J 9/1641; H02P 29/00; A61B 5/1121
(Continued)

(56) References Cited

U.S. PATENT DOCUMENTS

| 4,943,468 A * | 7/1990 | Gordon | ................ H05K 1/0306 |
| | | | 174/258 |
| 8,840,570 B2 * | 9/2014 | Branch | ................ A61B 5/1121 |
| | | | 600/587 |

FOREIGN PATENT DOCUMENTS

| JP | A1977009785 | 1/1977 |
| JP | A1987150405 | 7/1987 |

(Continued)

OTHER PUBLICATIONS

International Search Report on corresponding PCT application (PCT/SE2013/051224) from International Searching Authority (EPO) dated Mar. 27, 2014.
(Continued)

*Primary Examiner* — Bentsu Ro
*Assistant Examiner* — Zemenay Truneh
(74) *Attorney, Agent, or Firm* — Klein, O'Neill & Singh, LLP

(57) ABSTRACT

The invention relates to a method for determining at least one property of a joint, such as a joint (112, 114, 116-119, 180) of a manipulator (110), wherein said joint is configured to be driven by at least one actuator, the actuator being configured to drive said joint (112, 114, 116-119, 180) via a drivetrain. The method comprises: clamping (200) said joint such that motion of the joint becomes constrained, and actuating (210) said drivetrain while monitoring at least one quantity associated with a torque of said actuator and at least one quantity associated with the actuator position in order to determine (220) at least one output value of said actuator,
(Continued)

said output value corresponding to at least one joint position and determining (230) the at least one property of the joint based on said at least one output value. The invention further relates to a system for determining the at least one property of a joint.

18 Claims, 10 Drawing Sheets

(51) Int. Cl.
  *G05B 19/042* (2006.01)
  *B25J 9/16* (2006.01)
  *H02P 29/00* (2016.01)
  *A61B 5/11* (2006.01)

(52) U.S. Cl.
  CPC ... *A61B 5/1121* (2013.01); *G05B 2219/40381* (2013.01); *G05B 2219/41059* (2013.01)

(58) Field of Classification Search
  USPC .......................................... 318/569; 600/587
  See application file for complete search history.

(56) References Cited

FOREIGN PATENT DOCUMENTS

| JP | U1993003697 | 1/1993 |
|---|---|---|
| JP | A1994222817 | 8/1994 |
| JP | H06222817 | 8/1994 |
| JP | H08152910 | 6/1996 |
| JP | 2005001013 | 1/2005 |
| JP | A2006101605 | 4/2006 |
| JP | 2009198203 | 9/2009 |
| WO | WO2012/076038 | 6/2012 |

OTHER PUBLICATIONS

Tri et al.; "Modeling torque-angle hysteresis in a pneumatic muscle manipulator"; Advanced Intelligent Mechatronics (AIM); 2010 IEEE/ASME International Conference; Piscataway, NJ, USA; Jul. 6, 2010; pp. 1122-1127; XP031855771; ISBN: 978-1-4244-8031-9.

Ruderman et al.; "Modeling and identification of elastic robot joints with hysteresis and backlash"; IEEE Transactions on Industrial Electronics, IEEE Service Center; Piscataway, NJ, USA; vol. 56, No. 10; Oct. 1, 2009; pp. 3840-3847; XP011267652; ISSN: 0278-0046.

Ruderman et al.; "modeling and observation of hysteresis lost motion in elastic robot joints"; $8^{th}$ IFAC Symposium on Fault Detection, Supervision and Safety of Technical Processes; Sep. 5, 2012; pp. 13-18; XP055107591; ISSN: 1474-6670.

Bennett et al.; "Kinematic calibration by direct estimation of the Jacobian matrix"; Proceedings of the International Conference on Robotics and Automation, Nice, France; May 12-14, 1992; Los Alamitos, IEEE Comp. Soc. Press, US; Volume Conf. 8; pp. 351-357; XP010027936; ISBN:978-0-8186-2720-0.

Office Action on corresponding foreign application (JP Application No. 2015-537664) from the Japanese Patent Office dated Apr. 19, 2016.

Office Action on corresponding foreign application (JP Application No. 2015-537664) from the Japanese Patent Office dated Dec. 13, 2016.

* cited by examiner

METHOD AND SYSTEM FOR DETERMINATION OF AT LEAST ONE PROPERTY OF A JOINT

CROSS-REFERENCE TO RELATED APPLICATION

This application is the National Phase, under 35 U.S.C. §371(c), of International Application No. PCT/SE2013/051224, filed Oct. 21, 2013, the disclosure of which is incorporated herein by reference in its entirety.

FEDERALLY SPONSORED RESEARCH OR DEVELOPMENT

Not Applicable

BACKGROUND

The present invention is related to a method and a system for determining at least one property of a servo-controlled mechanical motion such as a joint of a manipulator.

Robots have found wide application in many areas of industry. In particular, some industrial areas involve performing tasks dangerous to human health or labor performed under conditions not possible for humans to withstand. Other areas of industry involve repetitive tasks which can be performed much more efficiently and precisely by a robot.

An industrial robot typically comprises a manipulator devised to manipulate or process work-pieces and materials. The manipulator normally has an arm-like arrangement consisting of a series of segments, each of which is referred to as a link. Movement of each of these segments is sometimes a combination of a translational movement and a rotation around an axis. In other cases, the movement consists exclusively of a translational or a rotational movement. Both of these movement variations give each link a mechanical degree of freedom around or along what in the following will be referred to as a joint. Variants of a joint, such as spherical joints, can be considered as combinations of these simple translational or rotational joints, and the formal equivalence of these types of joints is consistent with the concept of generalized coordinates present in robotics literature. Correspondingly, forces and torques are considered equivalent, as is also the case for positions and angles, respectively.

A joint is typically actuated by a servo-controlled motor, which is controlled via feedback from the measured motion of the motor. The motor actuates the joint via a drivetrain that comprises gears and other transmission elements for the reduction of motor rotation to joint rotation. For the purposes of this application, the term drivetrain is to be construed as excluding the motor. The purpose of the transmission elements is to reduce speed and thereby increase torque.

Drivetrains are superfluous in so called direct-drive robots, but, due to inherent problems this type of robots is ridden with, especially regarding the control stiffness during force interaction between an end-effector (tool) and the work-piece, almost all modern robots are built with a dedicated drivetrain for each joint.

An actuator is to be construed as a motor (with its outgoing shaft) or another type of device able to convert energy into a mechanical effect on the drivetrain. Although the drivetrain is not considered to be part of the actuator for the purposes of this application, the sensors for measuring the motor angle are. Their output value is referred to as actuator position. The joint angle is normally only measured via the actuator. For this reason, transmission elements need to be manufactured with high precision and quality so that the manipulator's motions will accurately correspond to the performed actuation. However, end customers are typically not willing to accept the price increase imposed by the use of high quality materials why the suppliers are forced to manufacture the manipulators with components in the lower price segment.

Most modern, industrial manipulators have six degrees of freedom (DOF), i.e. they have six pairs of rotational joints and links that are serially connected. The ultimate link ends with a tool flange or an end flange for mounting of the end-effector (tool). An alternative to direct mounting of the end-effector onto the flange is the use of a tool exchanger consisting of a manipulator part that is mounted on the end-flange of the manipulator and a tool part that provides a mounting surface for the respective tool. The two tool exchanger parts are detachable and may be locked in place by means of a locking mechanism that is actuated by e.g. pneumatics. This enables simplified change of the tool. An automatic change of the tool, i.e. without manual work involved, can then be accomplished by the robot docking to a selected tool that then is fixedly attached to the manipulator by means of the locking mechanism of the tool exchanger.

Movement of the manipulator can either be effected manually by an operator or automatically by performing instructions according to a user program that defines the robot task. In the latter case the manipulator is controlled by the user program loaded or entered into a controller that controls the manipulator guiding it to reach a programmed pose. Such a pose consists of a position and an orientation for the desired end-effector placement. Hence, the controller is the part of the robot that controls the movement of the manipulator, including its joints.

To support efficient specification of poses for the end-effector, either manually or in the user program, and possibly from CAD data, the controller contains a kinematic model of the manipulator. Such a model includes a model of the joints and the links and their geometric relations.

In robot applications, e.g. industrial robots in manufacturing plants, it is very valuable if the resulting physical pose, within certain tolerances, agrees with the programmed pose. If that is not the case, it means there is a deviation between the programmed pose and the physical pose. This deviation could occur either at a single location or at a plurality of locations along a path, or at any use of the robot. Managing deviations by the user via adjustments in the user program or by teach-in of (slightly deviating) programmed poses, limits the reuse of robot tasks and increases the cost for robot programming and deployment.

In the early age of robotics the major deviations were due to deficient control, but from the mid-1980:s and onwards robots deviate from their programmed motion mainly due to manipulator properties in combination with the lack of control compensation of drivetrain inaccuracies as reflected in the manipulator properties. More specifically, the controller often has a suitable structure and functionality but lacks the actual robot specific data for the individual manipulator to support such compensation. There is thus a need to address these drawbacks in order to minimize deviations between the programmed and physical motions.

Notwithstanding this, further causes for deviations from the programmed motion are known in the art. In particular, one such cause may be inaccuracies in the link and joint geometries, e.g. due to kinematic errors. Kinematic errors can be managed by kinematic calibration, which is usually available from the robot manufacturer. Another cause of deviation is related to inaccuracies in the joint and arm mechanics and/or control of the arm dynamics during high-speed motion, such as torque saturation due to joint-wise or multi-body effects. Normally, such deviations are managed by model-based control provided by the robot manufacturer. Yet another cause of deviations from a programmed pose stems from inaccuracies due to force interaction between the end-effector of the manipulator and the work-piece, but also due to gravity and other forces acting upon the manipulator. Such deviations are also related to joint dynamics around or along the joint motion due to compliance and tolerances of bearings and other joint parts such as the transmission elements of the drivetrain.

Several types of solutions exist which deal with measuring and identification of the types of sources of deviation mentioned earlier. Amongst these, measurements with optical tracking systems are the most common. One type of solution uses external calibration systems with external sensors detecting torque or position of the joints or of the end-effector. While applicable to large scale production facilities with a large number of robots, the cost of such external calibration systems often exceeds the cost of a single robot. In smaller scale production facilities relying on the operation of one or a few robots, such external calibration systems are not applicable due to prohibitive cost. One example of an external calibration system is described in WO2012/076038.

A slightly modified version of the calibration system of the above kind is presented in the article "Kinematic Calibration by Direct estimation of the Jacobian Matrix" by Bennet, Hollerbach and Henri (presented at ICRA, 1992, in Nice, France). In the article, parameters in a Jacobian matrix (expressing the dependence between endpoint velocities and joint velocities, or correspondingly for the forces/torques) for a robot are estimated by first clamping the robot in a predefined pose and then actuating the joints of the robot based on information from an external force/torque sensor attached to a tool flange close to the point of clamping. Alternatively, a rigid rod that is jointed at both ends, or some other mechanism that in a well-defined way restricts movement of the manipulator relative to the environment, can be used for constraining one or more degrees of freedom, but such that certain joint motions are possible also in the clamped configuration. Data obtained from a set of such actuations result in a set of matrices, which are used to calculate the kinematic parameters. But even with kinematic calibration being performed with a force/torque-based method involving clamping, the actuator-to-joint dynamics remains neglected. As a result, accuracy is reduced so that this method, involving clamping of the joint, is not used in practice. Moreover, due to the properties of the drivetrain for each joint, the deviations caused by dynamic forces and force interactions with the work piece remain uncompensated for in current industrial applications.

SUMMARY

On the above background, it is the object of the present invention to alleviate at least some of the problems currently present in the art.

More specifically, there is a need for a simplified and inexpensive way of accurately determining joint parameters for a robot for the purposes of calibrating the robot poses and motions.

According to one aspect of the present invention, it is proposed a method for determining at least one property of a joint, such as a joint of a manipulator, wherein said joint is configured to be driven by at least one actuator, the actuator being configured to drive said joint via a drivetrain, the method comprising:

clamping said joint such that motion of the joint becomes constrained, and actuating said drivetrain while monitoring at least one quantity associated with a torque of said actuator and at least one quantity associated with the actuator position, determining at least one set of output values of said actuator based on the monitored quantities, said set of output values being related to at least one joint position, and determining the at least one property of the joint based on said set of output values.

Here, the term joint properties is to be construed as encompassing the properties of the actuator-to-joint dynamics, corresponding to the information that so far has been too costly or too difficult to obtain for it to be of practical use in robot applications.

One advantage of the above method is that joint properties are determined directly from the robot manipulator itself, which makes calibration of the robot much cheaper than using previously known calibration techniques. These parameters can either be directly read out from position and torque signals of the robot itself (if both available) or be deduced from other signals and physical properties together with data from the measured actuator position obtained from existing motor signals or sensors. For instance, motor currents can be measured by sensors other than those providing a torque signal, whereas actuator position may be sensed via an existing motor angle sensor.

Some physical properties can be used for compensating deviations so that these do not occur physically. Physical properties can also be used for tuning the control related to carrying out the method with which they are obtained. One example of physical properties for performance tuning may be the frequency response of the motor currents related to the actuator torque that is used for joint actuation.

The above method may also comprise the steps of obtaining nominal kinematic parameters and updating the nominal kinematic parameters based on at the least one determined property of the joint determined according to the method steps described earlier. This has the advantage that errors in the kinematic model of the robot manipulator, due to inaccuracies in the manipulator joint(s), may be reduced compared to existing calibration techniques. In this fashion, calibration of the manipulator using the joint properties together with updated kinematic parameters yields higher accuracy of position and repeatability than using parameters from existing kinematic calibration only.

Another aspect of the present invention is related to a system for determining at least one property of a joint, such as a joint of a manipulator, comprising:

at least one actuator configured to drive said joint via a drivetrain, clamping means configured to constrain the motion of the joint, means for monitoring at least one quantity associated with a torque of said actuator and at least one quantity associated with the actuator position, means for determining at least one output value of said actuator, said output value corresponding to at least one joint position, and means for determining the at least one property of the joint based on said at least one output value.

In addition to previously stated advantages, one further advantage of such a system is that it makes it possible to determine joint parameters by means of the robot itself using drivetrain models obtained in connection with existing and readily available sensors and signals. These parameters can then be used directly to update user programs or indirectly to update the servo control of the manipulator joints for the specific robot model (or an individual robot, e.g. after a certain time of usage or wear) on which measurements have been performed. All this is done in a simple and relatively inexpensive way, since the only external item needed for the joint properties measurement is a clamping item, which is used for clamping a movable part of the manipulator in one or several points in the workspace of the robot.

Preferred embodiments of the present invention are set forth in the dependent claims.

BRIEF DESCRIPTION OF THE DRAWINGS

In the following, the invention will be described in detail with reference to the appended figures, where.

DETAILED DESCRIPTION

In the following, the term robot is defined as a combination of a manipulator configured to operate on work items and a controller controlling the motions of the manipulator and one or more joints of the manipulator. The following example embodiments of the invention should be regarded as for illustration purposes only and not as limiting the invention itself. For example, any (revolute or prismatic) joint motion that temporarily or permanently is servo controlled, or which in any other way can benefit from knowledge of drivetrain parameters, forms a technically equivalent system.

Figure 1A:
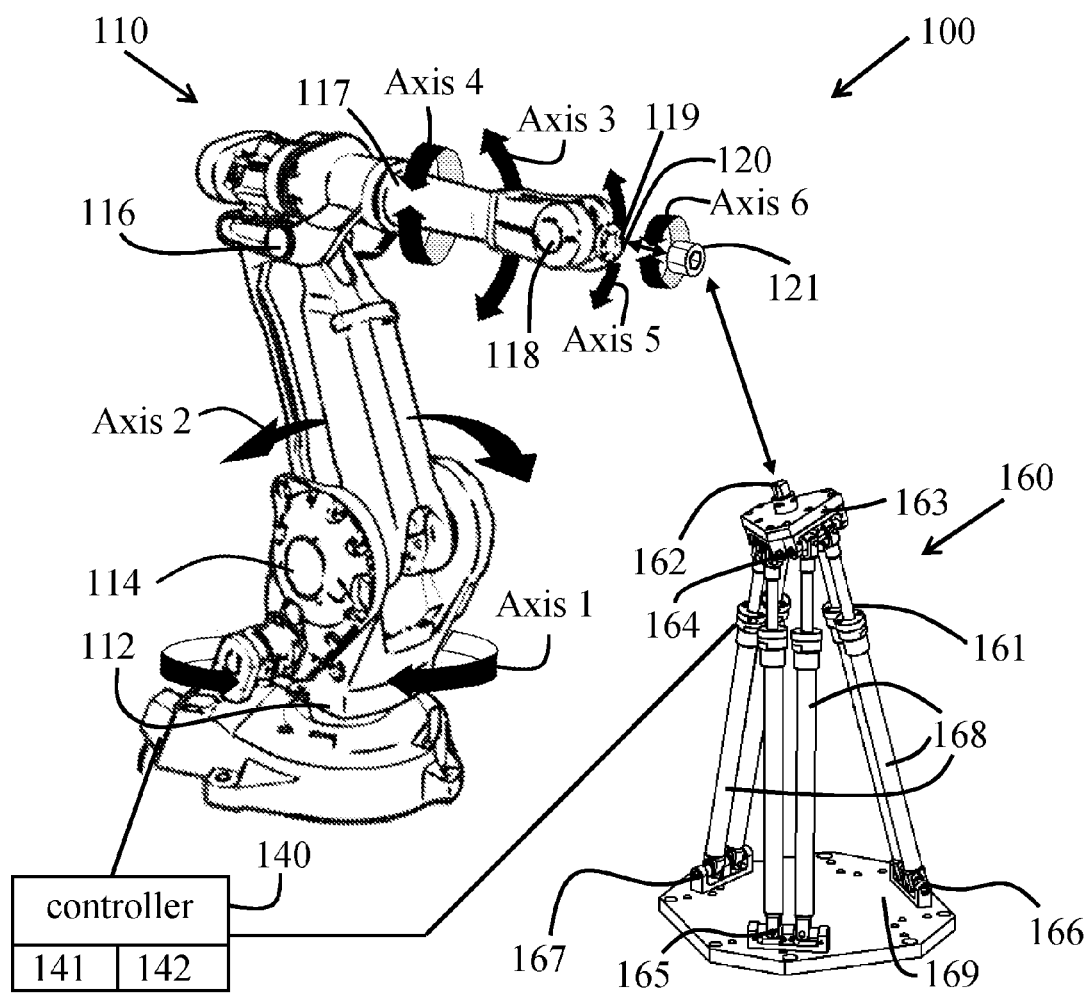
FIG. 1a depicts a system for determining joint properties of a manipulator according to one embodiment of the present invention.

FIG. 1a illustrates a system 100 for determining joint properties of a manipulator 110 using the clamping item 160. A controller 140 is devised to control the movement of the manipulator 110 and, optionally, of a clamping item. Depending on preference, the controller 140 may be external in the form of a manually or automatically operated control unit or a digital computer or internal, i.e. built-in into the manipulator 110 itself. Equivalently, the clamping item, or similar equipment for clamping of the selected movable part of the manipulator, is positioned manually or automatically (via the controller for the manipulator or through another control) such that the clamping of the movable part of the manipulator is accomplished.

As illustrated in the figures, the manipulator 110 comprises a number of joints 112, 114, 116, 117, 118 and 119 connecting different links of the manipulator in a fashion that is known to the skilled person. Each joint of the manipulator 110 is driven by a drivetrain (shown in FIGS. 1b and 1c and described below) actuated by a motor, such that motor rotations are translated into lower-speed rotations of the joins 112, 114, 116-119. It should be mentioned here that the system 100 may comprise any number of joints, i.e. one or a plurality of joints and that the number of manipulator joints is not critical for practicing the invention.

As mentioned earlier, the drivetrain may comprise gear wheels or other transmission elements. Most manipulators comprise built-in sensors, such as encoders or resolvers attached to the motor shaft or similar to sense the actuator positions of the joints, since, for one, the robot needs to know its position in relation to an internal coordinate system (spanning a joint space) and, secondly, to relate its position in relation to an external coordinate system (usually spanning a Cartesian space).

In the embodiment of the present invention in FIG. 1a the previously mentioned built-in sensors are used to determine joint properties for each of the joints 112, 114, 116-119 of the manipulator 110. Using the joint and Cartesian space analogy, parameters describing the actuator space, such as joint motor angles driven by force or torque, are translated into parameters describing the joint space, such as joint positions as known from kinematic calibration.

As is evident from FIG. 1a, the joints 112, 114 and 116-119 are arranged such that the manipulator 110 has six degrees of freedom (DOF) in total, where the DOF are illustrated by the thick arrows describing the directions of rotation around the rotation axes 1 to 6. Also presented in FIG. 1a is a tool mounting flange 120 onto which a manipulator side of a tool exchanger 121 can be mounted (shown detached for clarity), the latter fitting with the tool part of the tool exchanger (not shown) mounted on various tools (not shown), which permits changes of tool without manual assistance. This manipulator structure is frequently seen in industrial robots of today, but also other structures such as those of parallel-kinematic machines (PKMs) exist. Regardless of the kinematic structure, actuation and drivetrains work in a similar manner (although typically somewhat simpler in case of PKMs), and methods/systems for obtaining drivetrain model parameters are practically identical.

The system presented in FIG. 1a further comprises a clamping item 160 comprising a head 163 and three pairs of legs 168 attached to a base plate 169. It should be emphasized that the shape and structure of the clamping item 160 in the embodiment in FIG. 1a in no way should be interpreted as limiting the shape and structure of a clamping item to be used in the system according to the present invention. In fact, the clamping item 160 may have any structure or shape as long as it can provide a point in space for the manipulator 110 to be docked onto. Now, on top of the clamping item head 163, a protrusion 162 for docking corresponding to the tool side of the tool-exchanger is located, such that the protrusion 162 is reachable by the manipulator 110 and fitting with the corresponding manipulator side of the tool-exchanger 121. Additionally, the head 163 and one end of the three pairs of legs 168 are connected via joints 164, such that the head 163 may be rotated around one or more of the joints 164. Furthermore, the other end of the legs 168 may also be attached to the base plate 169 via the joints 165-167 each comprising their own rotational axes (not shown). With a fixed length of each of the legs 168 the clamping item head 163 is also locked. When releasing the locking bushings 161 of one or several legs, the clamping item head 163 is also released. Moreover, the locking of the bushings 161 can be controlled from the controller 140, such that the legs 168 (that in released mode are telescopic) of the clamping item 160 can be locked with different lengths. In this fashion the head 163 and thereby the protrusion 164 may be moved to virtually any point in space. Note however, that the clamping item 160 of the system 100 according to the present invention may have a much simpler structure and fulfil its function as a clamping item already if it can provide a point in space to which the manipulator 110 can be clamped. An advantage with the freely movable clamping item shown in FIG. 1a is that a multitude of clamped poses close to each other can easily be provided, which facilitates determination of drivetrain properties that might vary with internal tooth-wheel or bearing angles or similar details of the involved transmission elements.

Now, the embodiment of the invention in FIG. 1a with the clamping item head 163 corresponding to the tool side of a tool exchanger (not shown) utilizes the principle that a change of an end-effector can from a tooling point of view be considered equivalent to a manipulator docking with a clamping item. The change can be performed either manually or automatically, whereby the latter case corresponds to a robot being programmed to change its end effector by using the tool exchanger to connect to a tool in a tool stand. A manipulator 110 that is not equipped with a tool exchanger during its normal operation can be manually equipped with the same for the calibration stage specifically. Alternatively, items for clamping can be attached to manipulator links or onto some side of the end-effector. Hence, any robot manipulator can be calibrated.

In the present embodiment, the clamping tool is the clamping item 160 or more specifically the protrusion 162 located on the clamping item head 163. The protrusion 162 is configured to provide a point in space for the tool-exchanger 121 to dock onto. Since the clamping item head 163 is configured to be positioned within a wide range, it may provide a wide choice of possible points in space for the tool exchanger 121 to dock onto. The clamping point is according to one embodiment chosen such that rotational movement of the manipulator segments around each of the six axes may be uniquely identified, e.g. such that singularities are avoided. This is one way of performing determination of joint parameters for each of the joints 112, 114 and 116-119. However, according to another embodiment, one arbitrary position for the protrusion 162 is selected, such that a clamping point in space is achieved for the tool exchanger 121 of the manipulator 110 which may be a singularity. Even in this case, joint parameters for each of the joints may be determined in that the controller 140 is configured to move the manipulator out of the first clamping point in space into to a second and possibly third clamping point (and so on, not shown) and by calculating solutions to the joint dynamic equations for each of the clamping points in space, joint parameters for each of the joints 112, 114, 116-119 of the manipulator 110 may be uniquely determined. The controller 140 may for the same purpose also hold the manipulator 110 clamped to the clamping item 160, while moving the manipulator 110 to one or more further positions corresponding to a second or third or possibly even more clamping points in space.

It should be mentioned here that not only the protrusion 162 of the clamping item 160 may be used to dock the tool-exchanger 121 to a point in space, but that any part of the clamping item 160 to which the tool-exchanger 121 or any other part of the manipulator 110 can be clamped to reach a well-defined point in space can be considered sufficient to perform the clamping function. Now, while the one or more points in space to which the tool exchanger 121 may be clamped are uniquely defined, the pose which the manipulator achieves at this point in space may not be unique, since the manipulator may be controlled by the controller 140 to reach a plurality of mutual joint positions all of which may result in either the tool exchanger 121 or some other part of the manipulator being clamped to the same point in space provided by the protrusion 162 or some other part of the clamping item 160.

While the tool exchanger 121 is clamped onto one or more points in space, the controller 140 is configured to read out output values from the internal sensors of the joints of the manipulator 110. These values reflect drivetrain properties that may be translated into joint parameters, such as backlash, compliance and other possible parameters.

However, before the tool exchanger 121 is clamped onto one or more points in space, the controller 140 may be configured to determine kinetic and possibly viscous friction for each of the joints 112, 114, 116-119. Also, before the tool exchanger 121 is clamped, the manipulator 110 may be impacted and the controller 140 may be configured to determine resonant frequency or frequencies for the manipulator 110 from monitored torque and position for the one or more joints of the manipulator 110, and from the resonant frequency or frequencies determine a suitable bandwidth for the control of the clamping/clamped motions and for the monitoring of the joint actuator torque and joint position.

This will be explained in more detail in connection with the embodiments of FIGS. 5-7.

Now, according to one embodiment, the controller 140 is configured to read out joint motor torque and joint position directly from the internal sensor output for each joint. According to another embodiment, if the joint motor torque is not directly available, the controller 140 is configured to monitor other actuator quantities from which the motor torque can be indirectly calculated, such as motor torque control or torque observer dynamics based on other servo control states. Motor torque can also be obtained by measuring motor currents and computing the actual torque for the type of motor being used. However, the controller 140 can be expected to have the current joint position readily available, since industrial robots in most cases are equipped with corresponding position sensors.

It may also be established that by clamping the manipulator it is meant clamping of the movable part of the manipulator 110 to a point in space provided by the clamping item 160. The attachment of the other end (base part) of the manipulator to a ground plate or to the floor is not considered to be a clamping operation and will not be treated as such in this description. The base of the manipulator 110 and the base plate 169 of the clamping item 160 are to be rigidly connected to each other during the clamped motions, but the base parts can of course also be clamped to each other, e.g. by a mobile robot docking (not shown) to an environment with the base plate 169 rigidly attached to it.

Figure 1B:
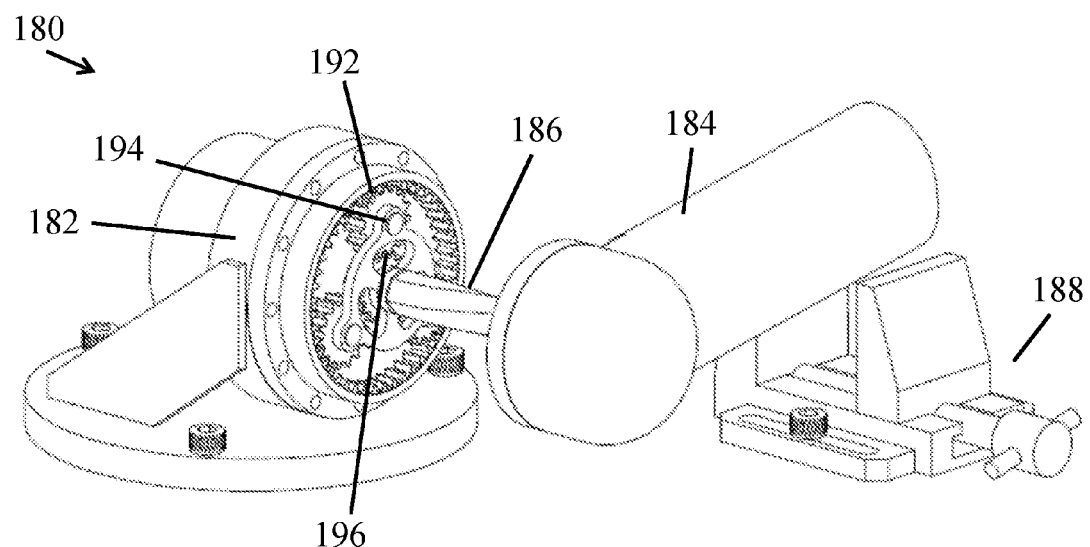
FIG. 1b shows a set-up for determining joint properties of a single joint, which is similar to a manipulator joint such as the one denoted Axis 2 in FIG. 1a, but for clarity purposes shown with an exposed drivetrain and a simple manual clamping item.
Figure 1C:
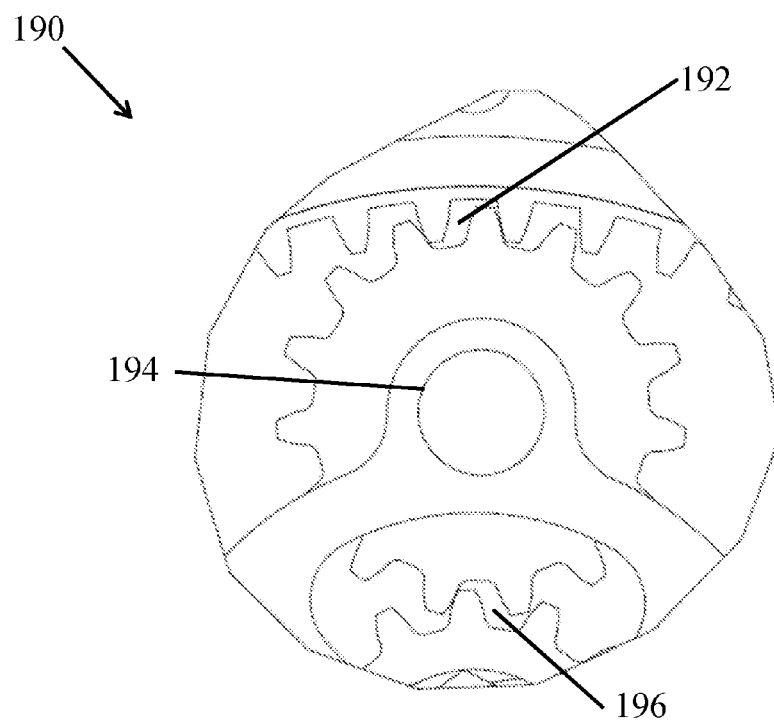
FIG. 1c is a close-up of a detail of FIG. 1b showing a plurality of tooth wheels belonging to the drivetrain that is part of FIG. 1b, with said tooth wheels being shown in engagement on one side and backlash on the other side.

A technically equivalent clamping situation can be accomplished for a single joint of the manipulator 110 by clamping a link to a fixed point in space. For instance, the manipulator 110 can have a part of a tool-exchanger attached to the front of the second link (the Axis 2 motion), which moves orthogonally to the preceding axis 112 (Axis 1) that therefore does not interfere with the clamping of joint 114. Furthermore, the joints 116-119 remain unclamped and not being part of the clamping of joint 114. As an alternative to docking with a tool exchanger on a clamping item 160, or to any other dedicated clamping item, off-the-shelf clamping equipment can be used. Still considering clamping of the joint 114, such a standard clamping item may be of the type shown in FIG. 1b with reference numeral 188. FIG. 1b shows such a joint with part of the drivetrain cover removed to expose the drivetrain transmission elements, which in this case is a planetary gearbox connecting the motor 182 via a compliant shaft 186 to the link 184. The link 184 effects the shaft 186 with the torque resulting from the gravity force of link 184, and the torsion of shaft 186 is visible by means of the twisted edge lines. If, for the sake of simplicity, friction and inertial forces are disregarded from for the time being, the gravity force is balanced by a motor torque acting over the drivetrain, and hence the corresponding sides of the tooth-wheel cogs are in contact as shown in FIG. 1c. Sources of backlash include tooth gaps 192, 196. Friction occurs at the bearing 194 and at other sliding or rolling contact between drivetrain transmission elements. While the torsion 186 may be linear, the compliance including the plate holding the planet wheels in combination with gradual tooth contacts normally results in a non-linear compliance property.

Together with the manual clamping item 188, the system 180 may be viewed as a joint of a manipulator. Equivalently, it may represent any one joint of any one servo-controlled mechanism. Thus, the clamping items 160, 188 are by no means restricted to the form and shape provided in FIGS. 1a and 1b, respectively, but may have any shape or form as long as they are essentially free from backlash and can provide a point in space for clamping of the movable part of the manipulator 110. Therefore, the clamping item may be elastic, such that the manipulator after initial clamping to the clamping item may reach a point in space in which it is clamped later, once it has achieved a resting position at the clamping item. In case of an elastic clamping item, the stiffness of the same should be known, and the elastic displacement of the clamping item will need to be determined based on tool exchanger forces, which in turn can be determined via joint torques and the kinematic model or by using an external wrist mounted force/torque sensor.

It should also be mentioned that the system for determining joint parameters of a manipulator according to the present invention also may comprise two or more robots, i.e. two or more manipulators using each other as clamping items each providing a clamping point in space for the manipulator of the other robot, such that joint properties for each joint in each manipulator can be determined for example according to the method of the present invention of which several embodiments are illustrated in FIGS. 2-7. In absence of a rigid and fixed point of clamping, a dual arm robot may require more poses and measurements to uniquely determine all joint parameters.

Moreover, the manipulator 110 of FIG. 1a, although portrayed as a single arm manipulator may equally be a dual-arm manipulator, where analogous to the description in the previous paragraph, the arms may be used as clamping items for clamping each arm to a point in space provided by the other arm for the purposes of determining joint properties for each joint in each arm. A dual arm robot can also clamp a link by letting the other arm with any suitable link push the link of the other arm against a rigid environment (or an environment with known compliance). Even in these cases join properties for each arm of the manipulator can be determined according to the method of the present invention of which several embodiments are illustrated in FIGS. 2-7.

Determination of at least one joint property will now be described with the help of FIGS. 2-7.

Figure 2:
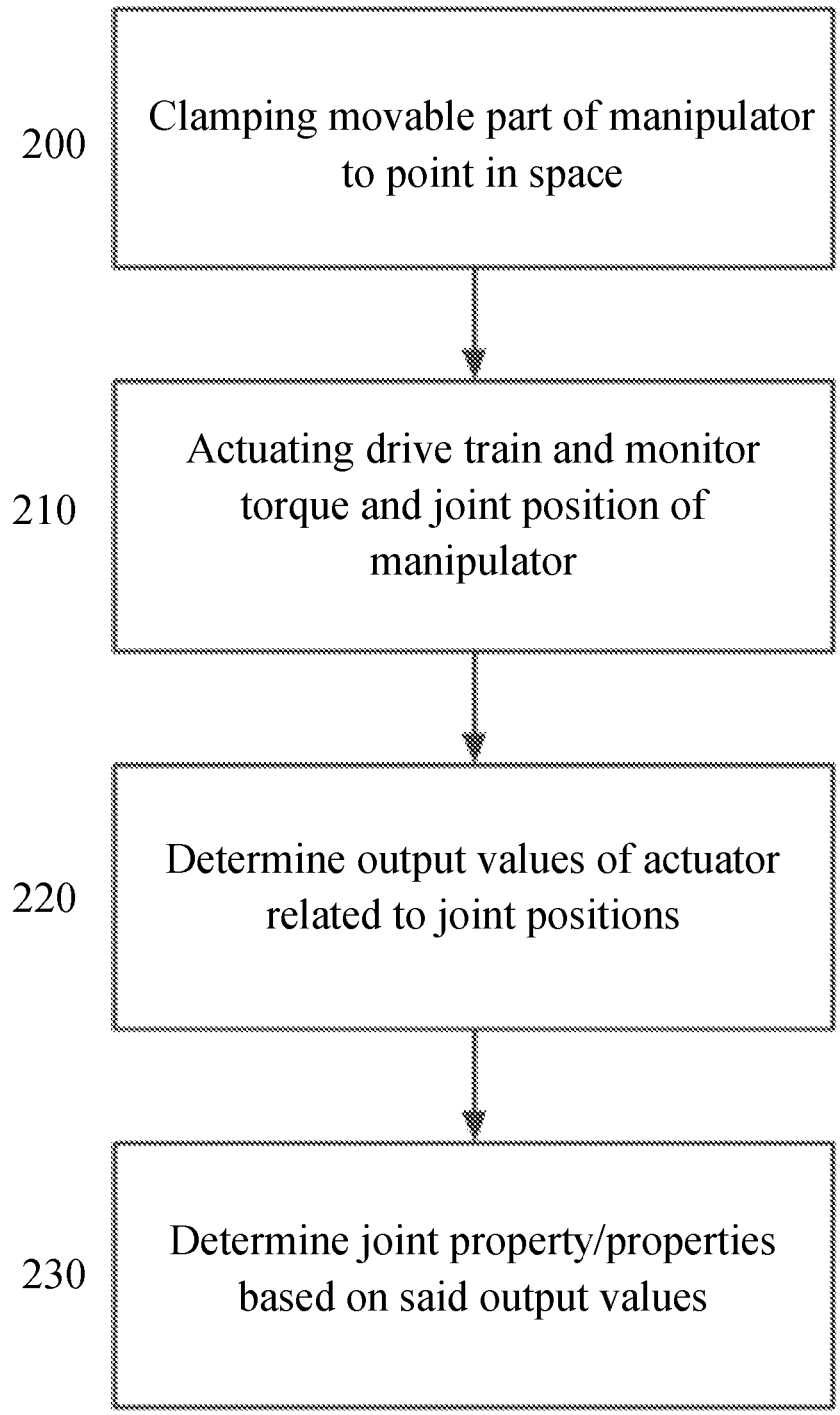
FIG. 2 depicts a flowchart of a method for determining joint properties of a manipulator according to one embodiment of the present invention.

FIG. 2 depicts a flowchart illustrating one embodiment of a method according to the present invention.

At step 200 the controller 140 instructs the actuators for each of the joints 112, 114, 116-119 of the manipulator 110 to move each joint such that the manipulator 110 docks to the point in space provided by the clamping item 160. This point in space may either be defined by the protrusion 162 of the clamping item 160 or by some other part of it. If the clamping item 160 is rigid, the clamping point provided by the clamping item 160 will be essentially the same as the point in space to which the tool exchanger 121 or some other part of the manipulator 110 has been clamped. Otherwise, in the case of a soft or elastic clamping item, the initial clamping point provided by the clamping item will differ from the point in space to which the tool exchanger 121 or some other part of the manipulator 110 is finally clamped. As mentioned earlier, either the controller 140 may instruct the actuators for each joint 112, 114, 116-119 to move the joints, such that the manipulator 110 reaches the contact point provided by the clamping item 160, or the controller 140 may cause the clamping item 160 to move (e.g. by releasing the locking bushings 161 of the links 168 and having the manipulator 110 docked and moving the protrusion 162, all according to instructions in a robot user program loaded into the controller to automate the entire calibration procedure) in order to accomplish the docking/clamping of the tool exchanger 121 or some other part of the manipulator 110.

In each of the above mentioned cases, the manipulator 110 will now have reached a well-defined point in space to which it remains clamped in a specific pose. This pose may be a starting point to uniquely determine joint parameters for each joint in which case a single point in space is sufficient. Otherwise, if the point in space is unsuitable for determining properties for two or more joints, the controller 140 may instruct the manipulator 110 or the clamping item 160 to move to one or more points in space from which joint parameters may be determined. Thereby it is possible to uniquely determine joint parameters for each of the joints 112, 114 and 116-119. The joint parameters of interest in this case are backlash and compliance, although other parameters may also be determined which may give sufficient information about the mechanical state of each joint.

Before proceeding with the method steps 210-230 it should be mentioned that for the sake of better understanding the method, steps 210-230 will be performed on one joint only. It is however possible for the controller 140 to transmit signals to the actuator to actuate drivetrains for each of the joints 112, 114, 116-119 and perform the steps 210-230 for each joint. As an alternative and depending on the kinematic structure of the manipulator, steps 210-230 may be performed for two or more joints in parallel.

In order to facilitate the comprehension of the invention at hand, the detailing of steps 210-230, as visualised in FIGS. 2-7, is based on specific control sequences that each results in a determined parameter of a joint with more-or-less ideal properties. Thereafter, a practically modified approach is described with references to FIGS. 8b-8e. That modified approach is a practical way of determining the joint properties when the controller 140 restricts direct control of the actuator torque. If access to the torque control is permitted, as for the provider of the manipulator, the following specific control sequences offer an explicit way of using the method.

Returning to FIG. 2, at step 210, the controller 140 transmits signals to the actuator to actuate the drivetrain for one of the joints 112, 114, 116-119 while keeping the manipulator 110 in the clamped position on the clamping item 160 defining the point in space mentioned earlier. At the same time, the controller 140 monitors the joint motor torque and joint position for one of the joints 112, 114 and 116-119 of the manipulator 110.

At step 220, the controller 140 selects and registers output values for the motor torque which correspond to certain joint positions of interest for obtaining the properties of one of the joints 112, 114, 116-119 of the manipulator 110. One example of such output values for the motor torque and joint positions may be joint positions in which the motor torque is essentially zero.

Finally, at step 230 the controller determines the desired joint property or properties from the output values and joint positions registered at step 220. The joint property or properties may be backlash, compliance or other joint properties alone or in combination.

Figure 3:
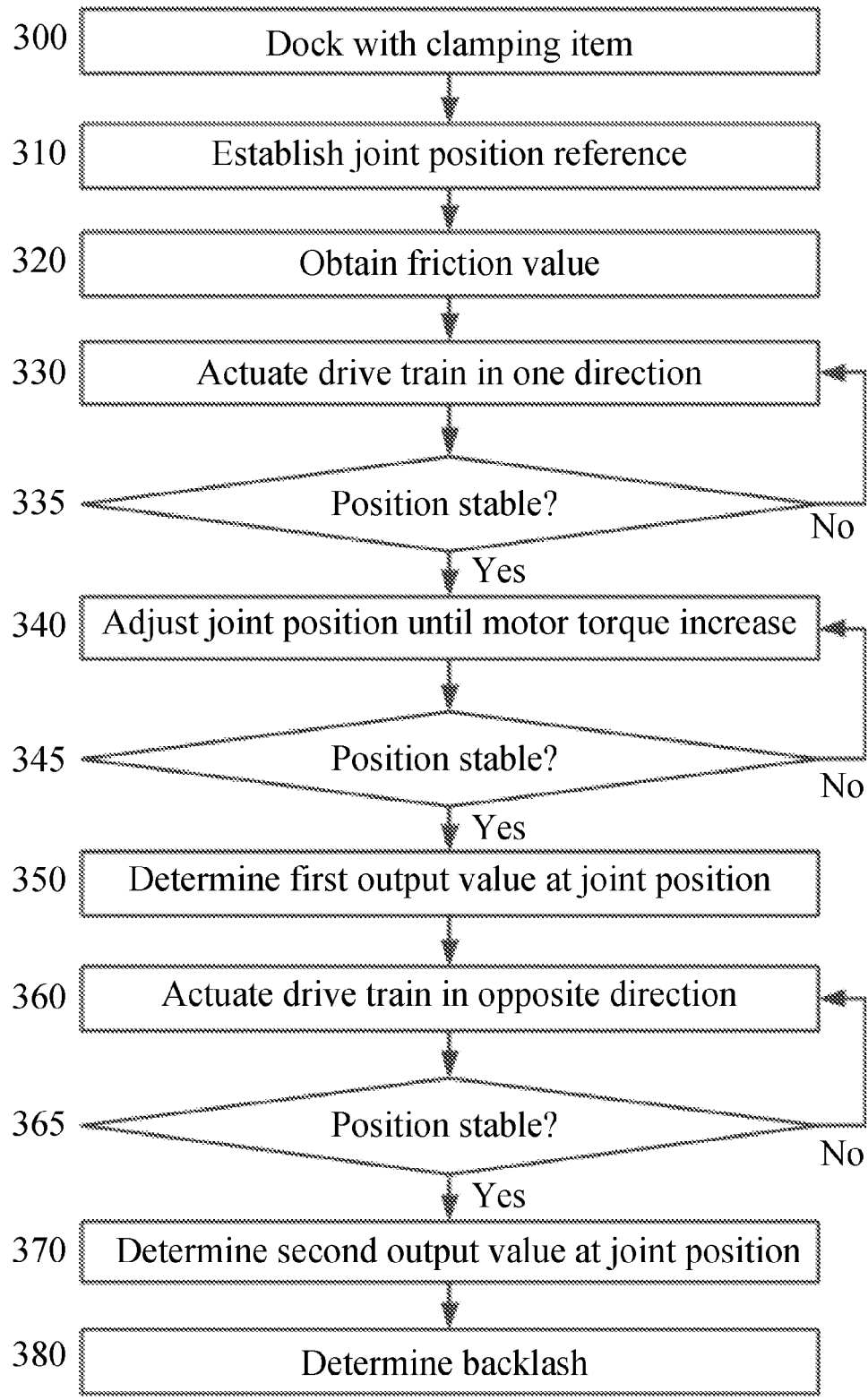
FIG. 3 depicts a flowchart of a method for determining joint properties of a manipulator according to one other embodiment of the present invention.

FIG. 3 illustrates another embodiment of the method according to the present invention in which the controller 140 determines backlash for the drivetrains driving the joints 112, 114 and 116-119. As in the previous method embodiment, the method embodiment in FIG. 3 is explained for one of the joints 112, 114 and 116-119 of the manipulator 110.

At step 300 the controller 140 instructs the actuators for each of the joints 112, 114, 116-119 of the manipulator 110 to move each joint such that the manipulator 110 docks to the point in space provided by the clamping item 160. This step is identical to the step 200 in the method embodiment illustrated in FIG. 2 and will not be elaborated further.

At step 310 the controller 140 enters a running position control and if needed (due to controller issues such as fault detection) adjusts a position reference for the joint such that a steady state position with acceptable torque is reached.

At step 320 the controller 140 obtains a kinetic friction value for one of the joints 112, 114-116-119. Here the kinetic friction value may simply comprise a kinetic friction previously known from measurements performed before the manipulator 110 clamped to the clamping item 160 or also comprise kinetic friction values after the manipulator 110 is clamped to the clamping item 160. In the latter case, the flowchart may include the sub-steps (not shown) of:
- the controller 140 transmitting signals to the actuator to move the joint motor in two opposite directions and monitoring the joint motor torque;
- the controller 140 estimating kinetic motor friction by obtaining a minimum sum of the motor torque in both motor directions;

using the torque value as a kinetic motor friction parameter.

At step 330 the controller 140 transmits signals to the actuator such that the drivetrain adjusts the joint position reference. The position adjustment of the joint can be achieved by the controller 140 by incrementing and decrementing the commanded/programmed joint control reference, which in case of a too low resolution may call for detuning of the motor control in order to obtain a smooth torque signal.

At step 335, the controller 140 checks whether the joint has reached a steady-state position, i.e. the joint motor speed and torque are essentially zero even if gravitational force is present.

If not, the method returns to step 330 where the controller 140 continues to transmit signals to the actuator to keep moving the drivetrain and thereby adjusting the joint reference position.

If yes, the controller 140 signals at step 340 to the actuator to actuate the drivetrain in order to adjust the joint position reference until the joint motor torque starts to increase. The position adjustment of the joint can be achieved by incrementing and decrementing the commanded/programmed joint reference drivetrain for one of the joints 112, 114, 116-119 in one direction until contact between the elements of the drivetrain, such as gear wheels, is established. Due to integral action in the manipulator servo control in combination with the limited stiffness of the drivetrain, the joint motor torque will stabilize on a level significantly higher than the friction.

At step 345 the controller checks whether the drivetrain position is stable, i.e. whether the gear wheels (if that mechanism is used for the drivetrain) of the drivetrain have reached contact.

If not, the method returns to step 340 where the controller 140 continues signaling to the actuator to keep actuating the drivetrain.

If the controller detects a stable position for the drivetrain, i.e. contact, the controller 140 registers at step 350 a first output value for the joint motor, which in this case is the motor angle X1 of the joint motor.

At step 360 the controller 140 signals to the actuator to actuate the drivetrain such that the drivetrain moves in a direction opposite to the direction at step 330. This may be implemented by the controller 140 by signaling to the actuator to actuate the drivetrain in order to decrement the position reference in a way analogous to step 340.

At step 365 the controller 140 checks whether a stable position for the drivetrain has been reached, i.e. whether contact between the gear wheels (again depending on the implementation) of the drivetrain has been achieved on the other side of the backlash.

If not, the method returns to step 360 where the controller 140 keeps signaling the actuator to actuate the drivetrain in the opposite direction.

At step 370, the controller 140 registers a second output value at the stable position, which in this case is a motor angle X2 of the joint motor obtained after N decrements relative to the stable position in step 345.

Finally, the controller 140 determines the backlash at step 380 for the joint drivetrain from the difference value $\Delta = X1 - X2$. If N is small (1 or 2) the backlash may be practically zero or the resolution of the incremental motions may be insufficient. In the latter case, detuning of the motor control can be applied in analogy with the procedure in step 330.

If the procedure was implemented on the user-programming level, the robot manufacturer has to provide a system-level interface or implementation that may have a much higher resolution than available to the normal robot programmer. Optionally, on some systems, the integral action in the servo control can be disabled or limited such that the smoothness of the data is improved and the then dominant proportional action can be tuned for a suitable torque effect.

It should be mentioned that under quasi-static conditions (slow motions), the input (mechanical) torque to the drivetrain from the (e.g. electric) motor torque of the actuator is the motor torque minus the kinetic friction. Since the commanded actuator motion is known and there is essentially no motion of the drivetrain output due to the clamping, this means that the drivetrain input torque can be controlled during clamped motions. That in turn implies that while determining the backlash in the clamped state this can be done based on the (motor-friction compensated) drivetrain input torque, or equivalently, the backlash identification principle can be formulated as if there was no friction (under the assumption of slow but non-zero motions).

Figure 4:
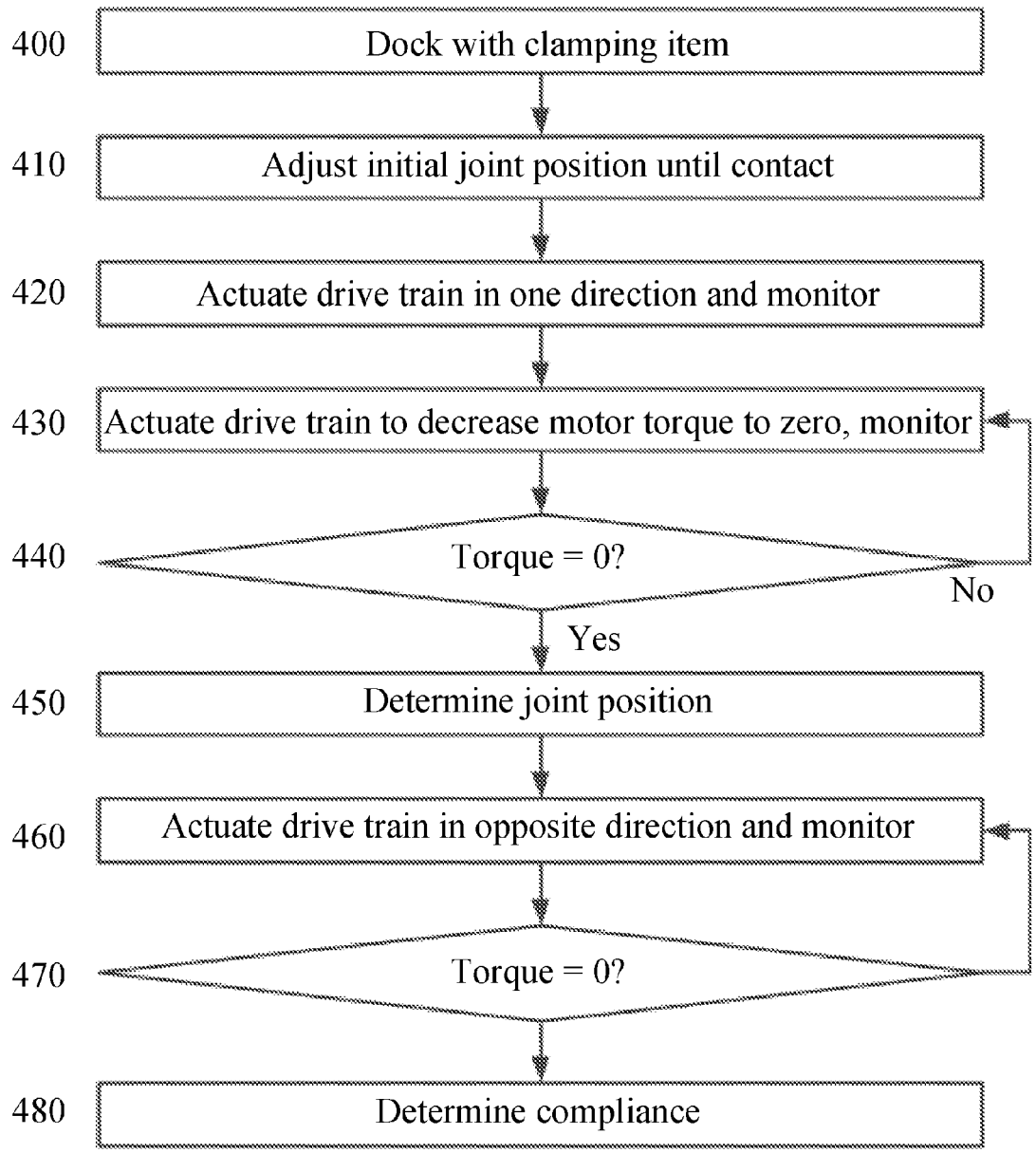
FIG. 4 depicts a flowchart of a method for determining joint properties of a manipulator according to yet another embodiment of the present invention.

FIG. 4 illustrates yet another embodiment of the method according to the present invention where compliance for one or more of the links of the manipulator 110 is determined.

Compliance can be defined as a lack of stiffness that every drivetrain exhibits. Compliance in each link (usually a small part) is by default identified as a joint compliance.

As in the previous method embodiments illustrated in FIGS. 2 and 3, the method embodiment in FIG. 4 will be illustrated using only one of the joint motors (not shown) of the manipulator 110. Almost all robots today have their main compliance in the drivetrain for each joint and thus this joint parameter is useful to determine.

According to the method embodiment in FIG. 4, if friction and backlash values for the joint are known to the controller 140 or if the controller 140 has determined these values according to the steps described earlier, the controller 140 is configured to determine compliance for one joint according to the steps below:

At step 400, the controller 140 instructs the actuators for each of the joints 112, 114, 116-119 of the manipulator 110 to move each joint such that the manipulator 110 docks to the point in space provided by the clamping item 160. This step is identical to the step 200 in the method embodiment illustrated in FIG. 2 and will not be elaborated further.

At step 410, the controller 140 signals the actuator to actuate the drivetrain in order to adjust a joint position reference, if needed with modified control as for the above backlash determination, such that contact at one side of the backlash is established. If the drivetrain for a joint is implemented by means of gear wheels, such contact can be characterized as the contact between the gears of each wheel co-operating to drive the joint.

At step 420, the controller 140 signals the actuator to actuate the drivetrain in order to increase the contact torque by incrementing the joint position reference while the controller 140 at the same time monitors the joint motor torque and position while increasing the absolute values of both quantities.

At step 430, the controller 140 instructs the actuator to actuate the drivetrain such that from a high joint motor torque according to the previous step 420, the joint motor torque is decreased towards zero while the controller 140 at the same time monitors the joint motor torque and position. Due to the construction of most gearboxes the stiffness will increase with increased torque, and for instance a third degree polynomial can be fitted to the monitored joint motor torque and position data, which will have a hysteresis of twice the friction.

At step 440, the controller 140 checks whether the joint motor torque is essentially zero.

If not, the method returns to step 430, where the actuator is signaled by the controller 140 to continue actuating the drivetrain.

If yes, the controller 140 registers the joint position at step 450 and proceeds to step 460.

At step 460, the controller 140 transmits signals to the actuator to actuate the drivetrain in order to increase the joint position reference in the direction opposite to the one at step 420 and to monitor joint motor torque and position analogous to the step 420.

At step 470 the controller 140 checks again if contact between the gear wheels of the drivetrain is established.

If not the method returns to step 460, where the actuator is signaled by the controller 140 to continue actuating the drivetrain in the direction opposite to the in step 420.

If yes, the controller the controller 140 registers the joint position at step 470.

The two joint positions should for typical gearboxes be symmetric.

Together with the backlash and friction values, the determined compliance defines the joint properties according to FIG. 1, which cover the properties around the (drivetrain and joint) axes (Axes 1-6) of rotation. In FIG. 1 the rotation of the links around the joints is depicted by axes 1-6 and thick arrows. According to one embodiment, the method makes use of a force-torque sensor at the tool exchanger for verification or for improved accuracy (e.g. by force controlled motions).

Figure 5:
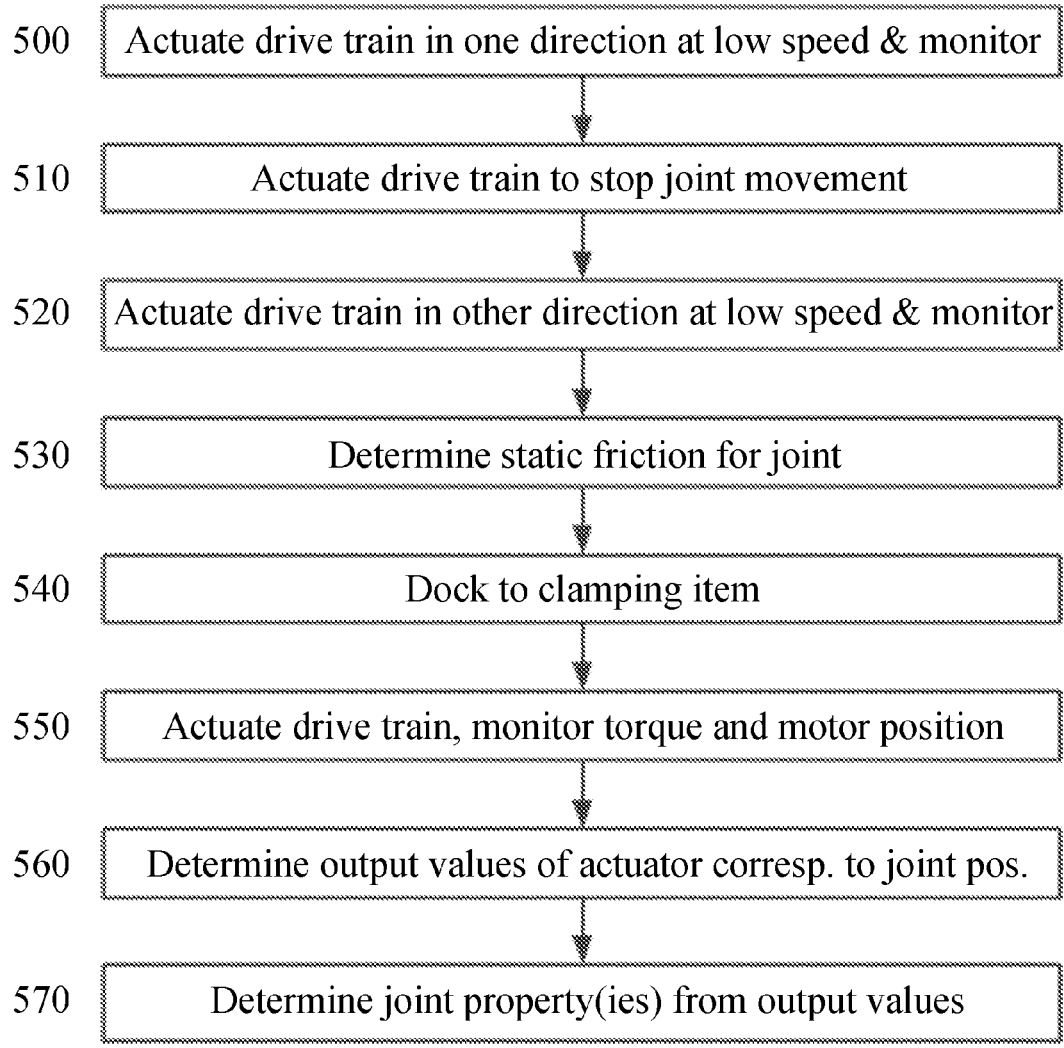
FIG. 5 depicts a flowchart of a method for determining joint properties of a manipulator according to another embodiment of the present invention.

FIG. 5 illustrates an embodiment of the method according to the present invention where kinetic friction for one or more joints 112, 114, 116-119 is unknown and needs to be determined by the controller 140. In this scenario, the kinetic friction is determined before the manipulator 110 is clamped to the clamping item 160.

At step 500, the controller 140 transmits signals to the actuator to actuate the drivetrain to move each joint 112, 114, 116-119 in one direction at low speed and observe the joint motor torque corresponding to the kinetic friction during the movement. Low speed in this context means moving the joint at a speed below a threshold speed value.

Thereafter, at step 510, the controller 140 transmits signals to the actuator to actuate the drivetrain to stop the movement of the joints 112, 114, 116-119.

Next, at step 520 the controller 140 transmits signals to the actuator to actuate the drivetrain to move each joint 112, 114, 116-119 at low speed in the opposite direction and observe the joint motor torque corresponding to the kinetic friction during the movement.

At step 530, the controller 140 detects a motor torque peak at the start as the kinetic friction and verifies/models any dependency on direction, temperature, gravity/load or any other condition that could affect the friction value.

The method then proceeds to steps 540-570 which are identical to the steps 200-230 in the method embodiment in FIG. 2 and will not be repeated here.

A normal industrial robot will have one static friction value per joint, which is close to the kinetic friction value for the joint. Mechanically, there could for some mechanisms be a significant difference, but under the influence of high-gain feedback control as for instance precise robots require there will be small vibrations due to sensor noise and a higher static friction is less of a problem. In any case, differences between static and kinetic friction is an issue to be dealt with in the low-level servo control, and is not part of the high-level compensation that the present invention deals with in terms of properties to be determined.

Whereas most robots have their main joint friction effect on the motor side of the drivetrain, some robots with much preloaded joint-side bearings or high friction sealing of the lubrication exhibit quite high joint side friction. By determining the kinetic friction of the joint both in free unclamped motion and in clamped motion, these two different kinetic friction parameters can be determined and distinguished from each other. The kinetic motor friction affects the joint before the backlash of the drivetrain, while the remaining joint friction affects the joint motion after those drivetrain parameters, which in obvious ways can be utilized within the compensation based on the joint properties. As is known in the art, such a high joint-side kinetic friction, in particular in the case of compliance but no backlash, is an indication that the hysteresis effect of kinetic friction in practice can be load-dependent, as the plotted monitored quantities in FIG. 8e show.

The controller 140 may also determine viscous friction for each joint in a manner similar to the steps performed for determining kinetic friction above also before the tool exchanger 121 is docked onto the protrusion 163 of the clamping item 160.

Figure 6:
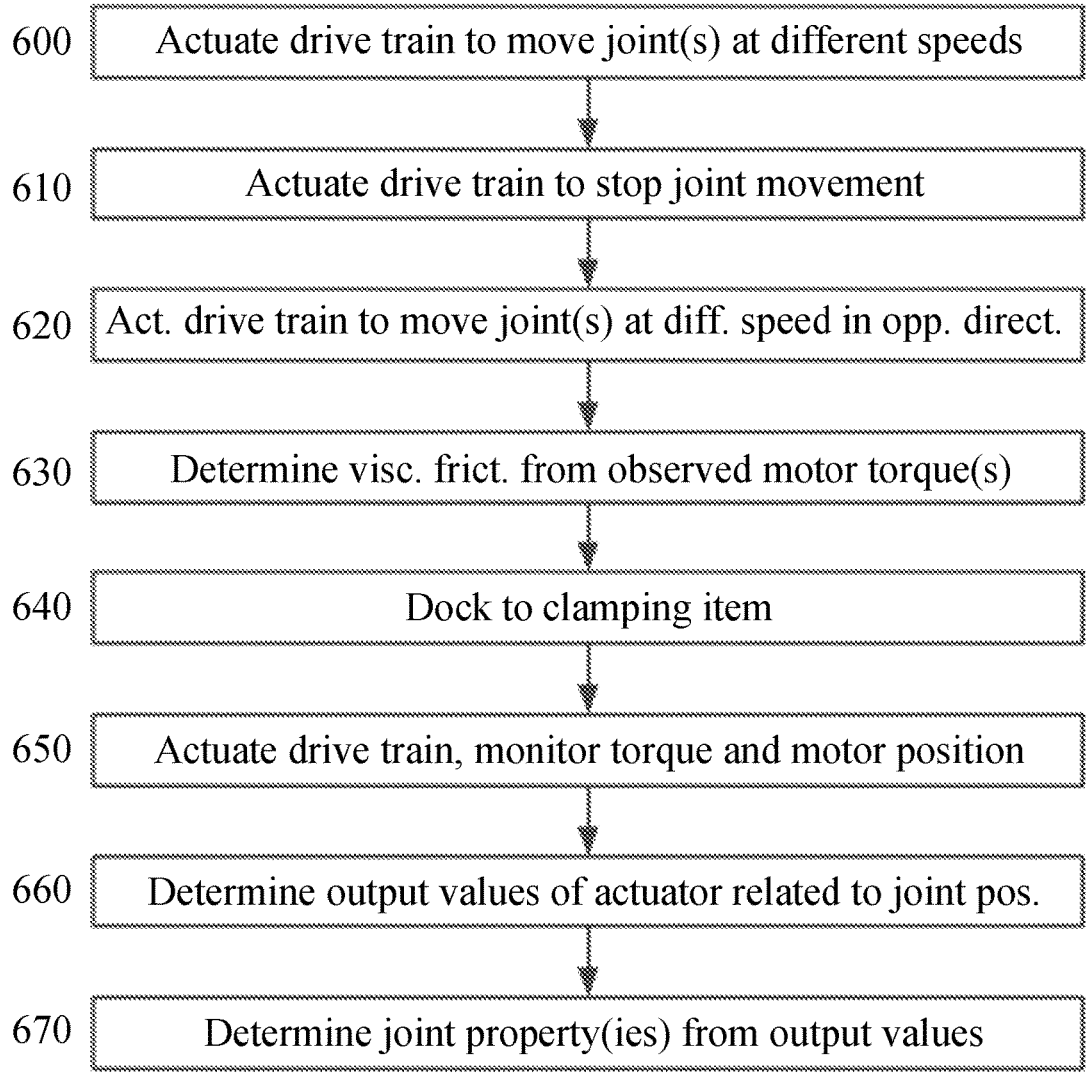
FIG. 6 depicts a flowchart of a method for determining joint properties of a manipulator according to yet another embodiment of the present invention.
Figure 7:
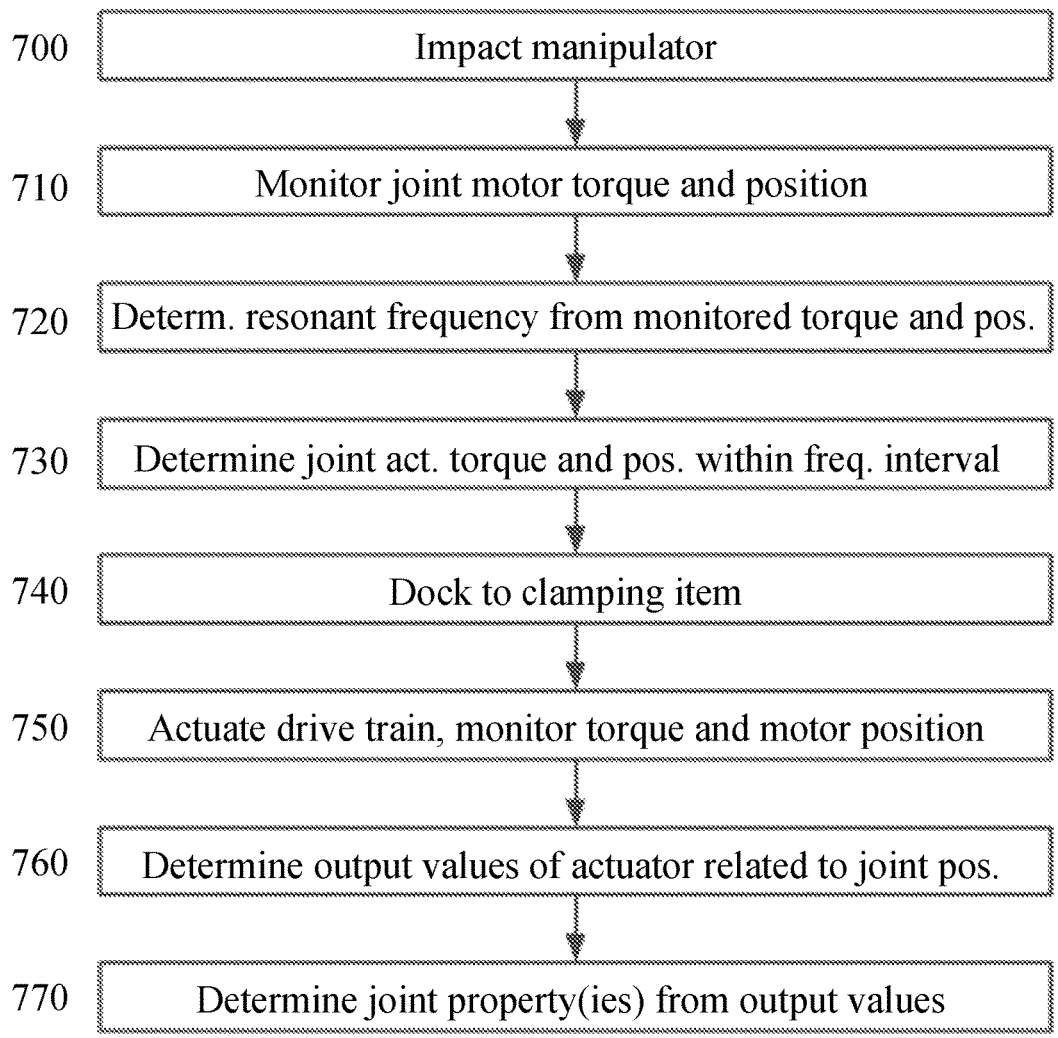
FIG. 7 depicts a flowchart of a method for determining joint properties of a manipulator according to yet another embodiment of the present invention.

One embodiment of the method where the kinetic friction is determined before the manipulator 110 is clamped to the clamping item 160 is illustrated in FIG. 6.

At step 600, the controller 140 signals the actuator to move one of the joints 112, 114, 116-119 in one direction at different speeds while the controller 140 monitors the joint motor torque during the movement.

At step 610, the controller 140 signals the actuator to actuate the drivetrain in order to stop the joint movement.

At step 620, the controller 140 signals the actuator to actuate the drivetrain in order to move the joint in the opposite direction again at different speeds which may be equal to the speeds at step 610 or different. At the same time the controller 140 monitors the joint motor torque during the movement in the opposite direction.

At step 630 the controller 140 then determines the viscous friction from the monitored motor torques during the joint movements in both directions.

Steps 640-670 are identical to the steps 200-230 in FIG. 2 and will not be elaborated further here.

One way of improving the performance of the method for determining joint parameters of which several embodiments have been described earlier in FIGS. 2-6 is to impact the manipulator 110 with an item. This embodiment is illustrated in FIG. 7

At step 700 the manipulator 110 is impacted either automatically or by the robot operator by some item, such that movement of all joints 112, 114 and 116-119 in all DOF is provoked.

At step 710 the controller 140 monitors the joint motor torque and the joint position for all the joints in the manipulator 110. This may usually occur during and after the impact at step 700.

At step 720 the controller 140 determines from the monitored joint motor torque and joint position for each joint 112, 114, 116-119 and especially for the joint with the biggest inertia a resonant frequency for the manipulator 110. The resonant frequency may be the frequency of the joint motor current registered during and after the impact of the tool exchanger 110 at step 700. The lowest resonance frequency gives an indication about the possible joint performance during the determination of the joint parameters mentioned earlier, such as friction, backlash and compliance.

At step 730 the controller 140 determines the joint motor torque and joint position interval corresponding to the lowest resonant frequency determined at step 720. It is in this interval that the controller 140 will determine joint parameters according to the method embodiments in FIGS. 2-6 described earlier.

Next, the method proceeds to steps 740-770 which are identical to the steps 200-230 described in connection with the method embodiment in FIG. 2. For that reason these steps will not be elaborated further.

The method embodiments in FIGS. 2-7 may also include the step of obtaining kinematic parameters (not shown) for the manipulator in order to determine the properties of the drivetrain dynamics for the manipulator 110. The controller 140 may comprise stored nominal (uncalibrated) parameters. Such parameters may instead be input to the controller 140 from datasheets. This step would precede the steps in the embodiments of the method according to FIGS. 2-7. Finally, after the joint properties for each of the joints 112, 114, and 116-119 have been determined according to the method embodiments illustrated in FIGS. 2-7, the nominal kinematic parameters may be updated based on the joint properties determined.

Figure 8A:
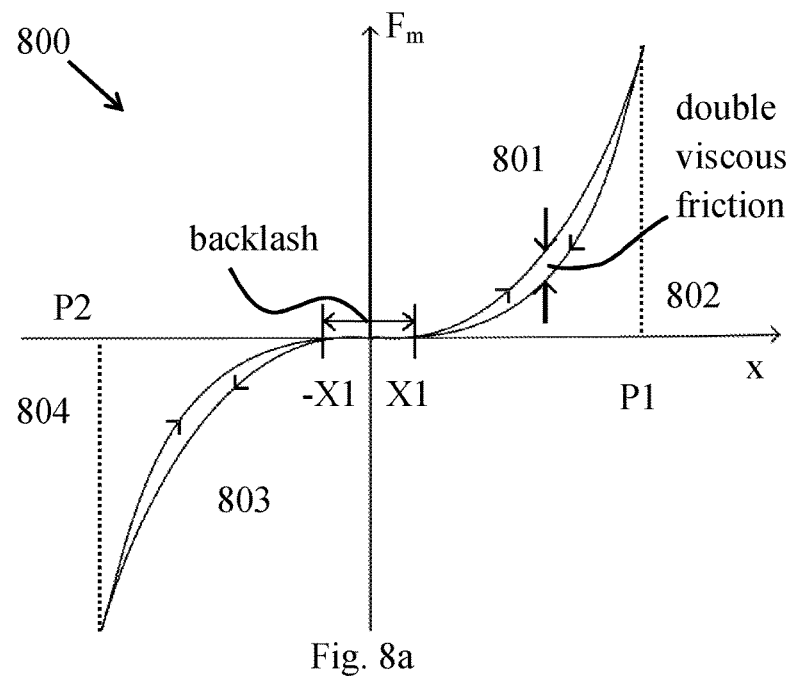
FIG. 8a shows a diagram illustrating the working of one embodiment of the present invention.
Figure 8B:
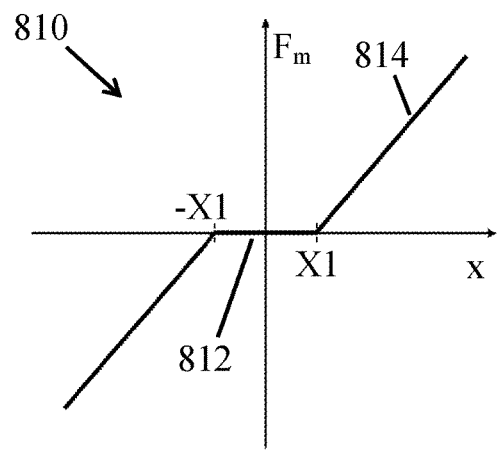
FIGS. 8b and 8c each show ideal backlash and lost motion, with the purpose of explaining those properties.
Figure 8C:
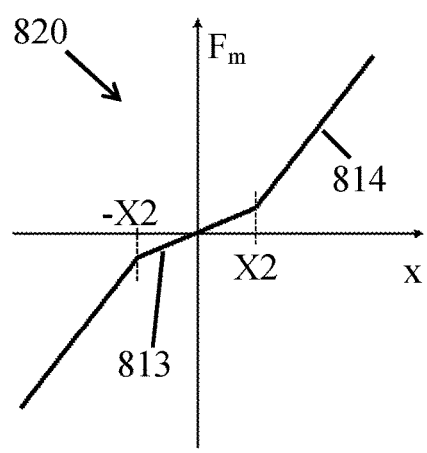

FIG. 8a illustrates a hysteresis diagram 800 for one joint of the manipulator 110 of a robot. The diagram illustrates joint motor torque $F_m$ as function of the actuator position x in the idealized case of essentially zero static and kinetic actuator friction but taking into account viscous friction of the drivetrain. Although the figure does not show the speed of motion, it is clear from the value of torque hysteresis during change of position x that the speed of motion is involved, and the end-points of the curve converge to the same value meaning that the kinetic friction value either is negligible or is cancelled by control-induced vibrations. Now, assume motions are quasi-static such that viscous effects are absent. While that implies slow motions, it is not a problem in terms of calibration time since the involved motion distances in clamped poses are very small. With a hysteresis curve as basis, the previously mentioned practically modified approach will now be more thoroughly discussed, with references to FIGS. 8b-8e that each contains at least one hysteresis effect.

The hysteresis curve shown in FIG. 8a shows a reciprocal motion between two positions, with an unloaded clamped position in between. Since the motor coordinate x anyhow is associated with an offset, for instance due to the mounting relative to the drivetrain, we can for the sake of simplicity select the offset such that the x coordinate is zero in the middle of the backlash, and then the contacts with the backlash are obtained at −X and X for a backlash of 2X. We can assume any direction of the hysteresis torque-position curve, for instance motion in the order 801-802-803-804 (or the opposite), but moving out of the backlash on both sides. This means that the actuating (210) the drivetrain is such that the motor, or equivalently the actuator, reciprocates between a first and a second position in opposite directions relative to the backlash range such that a fully developed drivetrain torque transmission is accomplished in both positions. Including the effect of kinetic friction, monitoring the actuator torque and actuator position results in a curve like the one in FIG. 8d. The solid line is the monitored motion in terms of the obtained torque-position cycle. Assuming the friction is symmetric, the average-value dashed line then represents the friction-compensated actuator torque that with its dependency on position captures position hysteresis, which in 8*d* is horizontally symmetric around the center of the backlash.

Figure 8D:
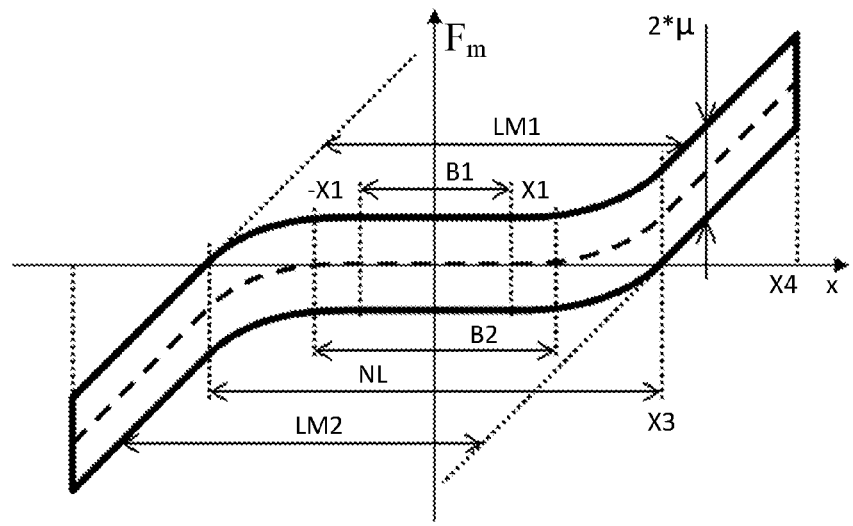
FIG. 8d shows an ideal hysteresis cycle as obtained from a compliant joint with backlash and ideal friction.
Figure 8E:
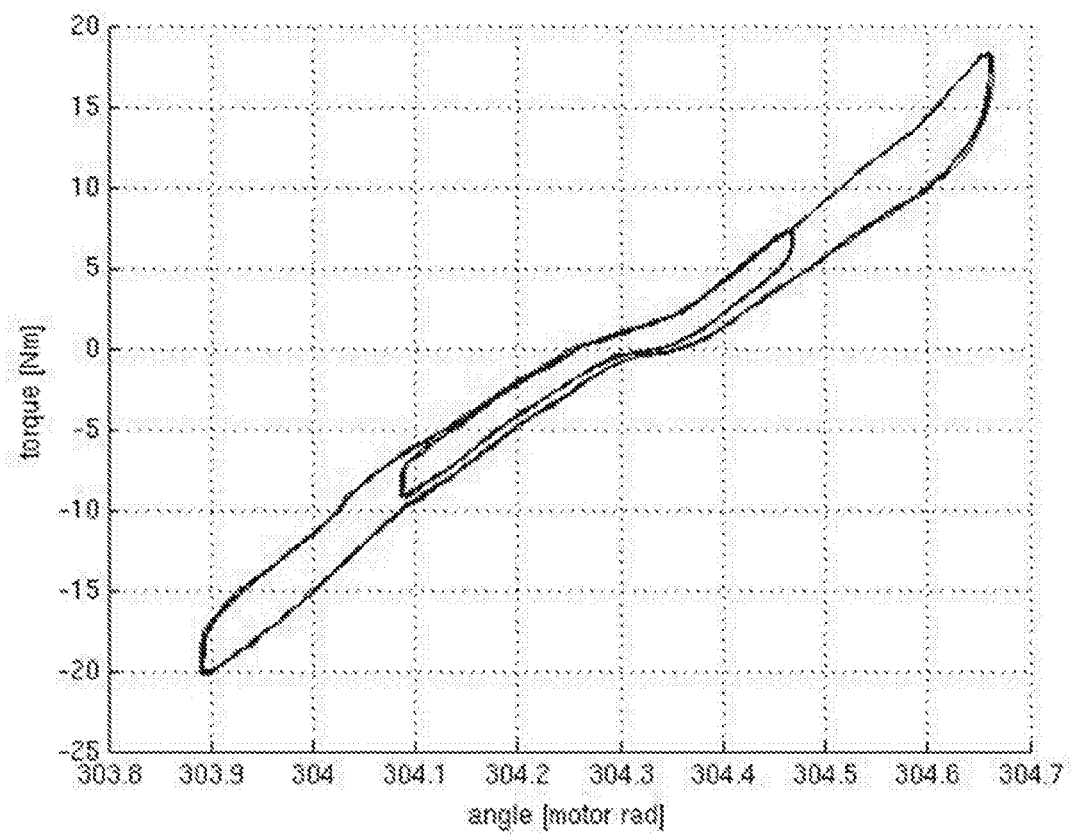
FIG. 8e shows two overlaid, real-life, thus non-ideal, hysteresis cycles obtained for different positions and therefore exhibiting different maximum torques.

The notion of a fully developed drivetrain torque depends on both the physical joint properties as such and on the intended use of the joint property to-be-determined. Two examples, illustrated in FIG. 8*d*, are the hysteresis in actuator torque respectively in position. These examples are briefly discussed in the following.

The torque hysteresis represents the kinetic friction, which is normally attributable to the actuator but for drivetrains with a plurality of elements there can be friction at different stages such as at the bearing 194. For a hysteresis cycle as the one in FIG. 8*d* and for certain reciprocal positions and certain maximum torques, the kinetic friction is constant, which means that there is a constant distance of $2*\mu$ between the upper and the lower curve, the kinetic friction being denoted $\mu$. As previously mentioned, the total kinetic friction can also be investigated in free-space motion. After determination of the friction property, which may be a function depending on also state capturing the torque history, the friction-compensated actuator torque can be determined. In the ideal case that is corresponding to the dashed line in FIG. 8*d*.

The position hysteresis to be used as a property of the joint, in case the hysteresis cycle looks like the one in FIG. 8*d* with a non-linear curve between X1 and X3, is different for high and low torques. For high torque we refer to the hysteresis as lost motion, which in each of the two directions of motion is marked LM1 and LM2 respectively in FIG. 8*d*. Here LM1 and LM2 are the same, but physically obtained values as in FIG. 8*e* show a variation. The friction-compensated dashed line can in the symmetric ideal case of FIG. 8*d* be used for determining lost motion as well. The backlash is the position hysteresis for essentially no drivetrain torque. In FIG. 8*d* there is zero (friction-compensated) torque over interval B1, but practically (from a sensing and control point of view) for low-load compensation it is more suitable to use the interval B2 as the backlash.

As discussed earlier, calibration and modeling methods known in the art have a decision problem in the definition of intervals, and an identification problem due to loading the drivetrain from the opposite direction compared to the actual servo control during use of the manipulator. The present invention, on the contrary, loads the drivetrain in the direction of the normal operation, and the definition of backlash (low torque) and lost motion (high torque) can be according to these intended use cases. Thus, the user of the present method can freely select the interval definitions suitable for the application or system at hand.

There is a similar decision to make concerning backlash and compliance, the latter being either non-linear as the curves outside B2 and within the NL interval in FIG. 8*d*. On this background and referring to different embodiments shown in FIGS. 8*a*-8*e*, two cases will be more thoroughly described in the following.

Firstly, the NL interval may be modeled by non-linear compliance outside B1 or outside B2. Secondly, if X1 (being the coordinate of the selected B1 or B2 interval) and X3 are close to each other we have the dashed line belonging to the case in FIG. 8*b* or 8*c*. However, it can be the case that there is no clear backlash 812 in between the compliances 814, and the model is instead that of FIG. 8*c* where a low-load compliance 813 is bridging the high-load compliances 814. The latter is a typical case when the drivetrain includes a pre-loaded gearbox, while the former is typical for simpler low-cost drivetrains. FIG. 8*e* shows two obtained hysteresis cycles with different maximum torques for a joint of a manipulator with a pre-loaded gearbox. Regardless of the obtained hysteresis cycle being ideal or not, the present invention includes the method to obtain it such that desired properties can be determined.

Carrying out the method as user of the manipulator 110 by programming or instructing the manipulator on a user-programming level of the controller 140 implies a limited access to setting the torques and position references, which in the digital controller 140 are discrete programmable quantities. For the obtained data to be representative for the physical properties, quantization effects need to be small. To that end, the robot manufacturer has to provide a system-level interface or implementation that may have a much higher resolution than available to the normal robot programmer. Alternatively and equivalently, manipulator controllers 140 normally allow for the integral action in the servo control to be disabled (or set to a value balancing the gravity torque), and then the dominant proportional action of the servo control can be tuned for a suitable torque effect with both smoothness of the monitored quantities and sufficient influence from the commanded position to the actuator torque. FIG. 8*e* was obtained in that way.

With reference to FIGS. 8*b*-8*e*, the practically modified approach to carrying out the method of the present invention will be detailed in the following.

As a fast and integrated procedure, the position reference of a joint is cycled in different ways, first in free space to determine various friction and gravity properties and then in clamped configuration to determine the other properties covering the drivetrain dynamics. During these cycles, the torque and position are monitored, and depending on controller properties the parameters of the control may be necessary to adjust for best accuracy. The properties of interest are then identified from the monitored signals, with obvious variations due to manipulator dynamics and controller properties. The entire determination of joint properties takes between one and a few minutes for all joints of a typical manipulator 110. To explain the method in more detail, however, the following description is based on a separation of the determination of different properties.

According to the method a joint 180, or equivalently a jointed movable part of a manipulator 110, is clamped 200 such that motion of the joint becomes constrained or locked, and the drivetrain driving the joint is actuated 210 by an actuator while monitoring at least one quantity associated with a torque of said actuator and at least one quantity associated with the actuator position. Then at least one set of output values of said actuator is determined 220 based on the monitored quantities, said set of output values being related to at least one joint position, and at least one property of the joint is determined 230 based on said set of output values.

According to one embodiment, the method further comprises obtaining hysteresis cycle data by actuating 210 said drivetrain such that the actuator reciprocates between a first and a second position such that fully developed drivetrain torque transmission, in opposite directions, is accomplished in both positions, whereas the monitored at least one quantity associated with the torque of said actuator and the at least one quantity associated with the actuator position make up the hysteresis cycle data, and wherein an initial joint position for said clamped joint is established prior to the actuation 210, and thereafter determining 220 said at least one set of output values of said actuator based on the obtained hysteresis cycle data.

While it is practical to obtain the hysteresis cycle data with actuator motions that are configured such that the reciprocal motions between a first and second point cover the entire torque range of interest, meaning that monitoring is done once during the entire motion and the different properties of interest are then determined by analysing the data afterwards without necessarily occupying the equipment such as the robot system 100, the constrained motion can also be performed as smaller dedicated experiments that together forms a technically equivalent method. The steps that are detailed by FIGS. 3-5 are to some extent examples of such dedicated experiments, but hysteresis cycle data can also be obtained in portions reflecting different parts of the cycle. For example, for a joint that during normal operation is always loaded with high gravity forces in one direction it could be sufficient to obtain the hysteresis cycle between the unloaded and the one side that represents the side with that direction of actuator torque. Consequently, a complete bidirectional hysteresis cycle can also be obtained in two parts around the unloaded clamped pose, and the determined properties of the joint can then be merged or used separately in the controller 140. Any such partial determination of the at least one property of the at least one joint is a special, and trivial, case that for brevity is not further commented. Also other variants involving the disclosed principles using the described quanteties, such as high-speed actuation of the drivetrain and then subtracting the viscous friction (e.g., obtained according to FIG. 6), forms a technically equivalent method.

The determined at least one property of the joint can be a lost-motion property, or lost-motion properties in case of an asymmetric hysteresis cycle, said method then comprising actuating 210 said drivetrain, within the permitted torque range, such that the fully developed drivetrain torque transmission is sufficiently high for a maximum position hysteresis to be obtained, and then determining 220 said lost motion based on the obtained position hysteresis. Moreover, as a way of averaging and identifying the lost motion based on the obtained torque-position data, the hysteresis cycle can be approximated by a curve, said method further comprising fitting two curves that asymptotically approach respective tail of the approximated curve where the actuator is moving such that the kinetic friction is fully developed. For at least one torque value, the lost-motion can then be determined as a position difference between the curves.

Another property that can be obtained from the hysteresis cycle data is backlash, which can be determined 230 from the position hysteresis by determining the difference in position for essentially the same drivetrain input torque such that said drivetrain input torque reaches an essentially non-zero value on both sides of the clamped position that is characterized by essentially zero drivetrain input torque. The determining 230 of the backlash can also be based on a determined drivetrain input torque obtained by compensating the actuator torque for an effect of friction prior to determination of the position hysteresis.

The method can also apply to a joint where the at least one property of the joint is a compliance of the joint, said method further comprising determining 230 the compliance by removing the effect of the obtained backlash from the hysteresis cycle data. Equivalently, the defined backlash interval, such as B1 or B2 in FIG. 8d, is considered when the compliance is determined. If the compliance is state-less with respect to the direction and previous loading of the drivetrain, it can be determined 230 by identifying a rate at which actuator torque increases and decreases as a function of increased and decreased actuator position. If that rate is the same on both sides of the clamped position, or if a single value for both sides needs to be used, a no-load/low-load compliance property can be determined by taking the average of the rates obtained for the essentially unloaded drivetrain. Correspondingly for higher drivetrain torques, the method can be applied for a fully loaded drivetrain, then obtaining a loaded-compliance property.

The notion of the compliance being state-less or not relates to whether or not the values from the monitored hysteresis cycle only deviate by an essentially constant value when the drivetrain torque is monotonously increasing or decreasing. In the state-less case a single compliance property function (over the NL interval in FIG. 8d) can be fitted to the unloaded and to the fully loaded compliance properties. In case of the hysteresis cycle being dependent on the maximum torque, such as in FIG. 8e, there is some state associated with the compliance property, and the compliance property function should have a state argument that reflects the needed effects, as previously discussed. Another example of possible compliance property states is related to lack of repeatability, for instance due to a drivetrain that is about to break or that is deficient in some other way. On the contrary, if the hysteresis cycle data is the same over several cycles with the same maximum load, the joint is of high quality for repeatable motions. This is the case in FIG. 8e, where each of the overlaid cycles actually comprises five cycles. Hence, that joint is of high quality for repeatability of compensated or uncompensated motions.

In another embodiment of the method the at least one property of the joint is a kinetic actuator friction, and its determining 230 comprises identifying a torque hysteresis from the hysteresis cycle data for at least one position value, wherein the value of the kinetic actuator friction is half the value of the identified torque hysteresis. Somewhat simplified, this friction property can also be referred to as coulomb friction. The static friction, and its difference from the kinetic friction being a measure of the risk for so called stiction, can be obtained during low-gain, slow-start of motions under clamped or unclamped conditions, but the motion during monitoring of the hysteresis cycle should be tuned such that stiction does not appear.

According to a further embodiment of the method, the hysteresis cycle can be monitored under different thermal conditions, where the actual thermal condition is represented by a measured and/or simulated temperature of the environment and/or of any of the mechanical elements of the joint, and the hysteresis cycle may be dependent on the temperature such that the determined properties vary with temperature. In such a case, it is straightforward procedure to determine a dependency of the at least one joint property with respect to temperature.

The method may further comprise repeating actuating the at least one actuator via the drivetrain in order to determine joint property values for at least two clamped joints. The method can also comprise a clamping configuration where the individual joints remain unchanged throughout the actuating 210 and monitoring phase.

The method can also include clamping of multiple joints and clamping of joints such that a manipulator 110 is clamped in one or several kinematic configurations, where in each configuration and for each joint the method embodiments may be applied.

Yet another embodiment of said method includes determining at least one property of a joint of a manipulator 110, said method comprising positioning a movable part of said manipulator at a clamping item 160, shown in FIG. 1a, within a work-space of the manipulator and contacting one point on the clamping item with said movable part and further comprising performing any of the method steps.

The method also comprises obtaining specific kinematic parameters by means of kinematic calibration of a manipulator, and updating kinematic parameters of the manipulator based on the at least one determined joint property. Thus, the manipulator may be better calibrated using the obtained at least one property. The kinematic parameters to be updated may be nominal parameters of the manipulator or kinematic parameters obtained with traditional calibration methods.

The disclosure also relates to use of the determined at least one property determined according to any of the method steps as disclosed herein, for updating nominal kinematic parameters of the manipulator. Further, the determined at least one determined joint property may be used for updating the actuation of the drivetrain of any controlled joint, for updating robot program poses to compensate for the determined deviations, or for updating motion control parameters of the manipulator based on the joint properties. Thus, the accuracy of the joint 180 or the manipulator 110 is improved, via updates of the controller 140, of the control unit 141, and of the instructions with robot poses that resides in the computer readable storage 142.

According to another aspect of the present invention, the use of the method is at least partly accomplished by a system for determining at least one property of a joint 112, 114, 116-119, 180, such as a joint of a manipulator 110, comprising at least one actuator configured to drive said joint via a drivetrain, clamping means configured to constrain the motion of the joint, means for monitoring at least one quantity associated with a torque of said actuator and at least one quantity associated with the actuator position, means for determining at least one output value of said actuator, said output value corresponding to at least one joint position, and means for determining the at least one property of the joint based on said at least one output value. The system further comprises at least a manipulator 110, said joint 112, 114, 116-119, 180 being a part of the manipulator, a controller 140 configured to control the manipulator, and clamping means 160 configured to enable docking and clamping of the end portion of the manipulator, such that the manipulator, when docked and clamped to the clamping means, attains a clamped pose.

The clamping means 160 can be a single tool exchanger at a fixed location in the work space of the manipulator 110. It can also be a manual clamping item for a plurality of joints or for a single joint 180 that can be clamped by a manual clamping item 188. The most suitable clamping item depends on the kinematic arrangement of joints, on joint properties, and on the need to automate the clamping as part of the method. A demanding case is when there is a need to clamp a plurality of joints that move in different directions, as for the manipulator 110, and when those joints need to be clamped in a plurality of positions very close to each other. As can be understood from FIG. 1*b*, a drivetrain may comprise a plurality of transmission elements that each can operate in a variety of angles/positions, which implies that the joint properties such as backlash 192, 196, can result in drivetrain properties that vary with actuator position, even for nearby positions. To determine such variations, preferably in an automated way due to the large number of clamping poses needed, the clamping item 160 permits automated and fine-grained positioning, which forms a final aspect of the system according to the present invention.

The invention further relates to a computer program (P), wherein the computer program (P) includes computer instructions for performing any of the disclosed embodiments of the method. Finally, the invention relates to a computer program product where the computer program (P) is recorded on a carrier, typically a computer readable medium 142.

In the drawings and specification, there have been disclosed typical preferred embodiments of the invention and, although specific terms are employed, they are used in a generic and descriptive sense only and not for purposes of limitation, the scope of the invention being set forth in the following claims.

The invention claimed is:

1. A method for determining at least one property of a joint (112, 114, 116-119, 180) of a manipulator (110), wherein said joint (112, 114, 116-119, 180) is configured to be driven by at least one actuator, the actuator being configured to drive said joint (112, 114, 116-119, 180) via a drivetrain, and a controller (140) configured to control motion of said joint (112, 114, 116-119, 180), the method comprising:
   (a) clamping (200) said joint (112, 114, 116-119, 180) such that joint motion becomes constrained;
   (b) actuating (210) said drivetrain, while monitoring at least one quantity representing a torque of said actuator and at least one quantity representing the actuator position sensed with a motor angle sensor, such that the actuator, by control of the controller, (140) reciprocates between a first position and a second position, and such that fully-developed drivetrain torque transmission, in opposite directions, is accomplished in both the first position and the second position, whereas the at least one monitored quantity representing the torque of said actuator and the at least one quantity representing the actuator position form hysteresis cycle data;
   (c) determining (220) at least one set of output values of said actuator based on the obtained hysteresis cycle data, said set of output values being related to at least one joint position; and
   (d) determining (230) the at least one property of the joint (112, 114, 116-119, 180) based on said at least one set of output values.

2. A method according to claim 1, wherein the at least one property of the joint is lost motion, said method further comprising:
   actuating (210) said drivetrain, within a permitted torque range, such that the fully developed drivetrain torque transmission is sufficiently high for a maximum position hysteresis to be obtained; and
   determining (220) said lost motion based on the obtained maximum position hysteresis.

3. A method according to claim 2, wherein the hysteresis cycle data are represented by an approximated curve having first and second tails, said method further comprising
   fitting first and second curves that asymptotically approach the first and second tails, respectively, of the approximated curve; and
   determining, for at least one torque value, the lost motion as a position difference between the first and second curves.

4. A method according to claim 1, wherein the at least one property of the joint (112, 114, 116-119, 180) is a backlash of the joint (112, 114, 116-119, 180) and the determining (230) of said backlash of the joint (112, 114, 116-119, 180) comprises:
   determining the maximum position hysteresis by determining the difference in position for essentially the same drivetrain input torque such that said drivetrain input torque reaches an essentially non-zero value on both sides of the clamped position that is characterized by essentially zero drivetrain input torque.

5. A method according to claim 4, wherein determining (230) of the backlash further comprises:
determining drivetrain input torque by compensating the actuator torque for an effect of friction prior to determination of the maximum position hysteresis.

6. A method according to claim 4, wherein at least one property of the joint (112, 114, 116-119, 180) is a compliance of the joint (112, 114, 116-119, 180), said method further comprising:
determining (230) the compliance by removing any effect of the obtained backlash from the hysteresis cycle data.

7. A method according to claim 1, wherein the at least one property of the joint (112, 114, 116-119, 180) is a kinetic actuator friction and the determining (230) of said kinetic actuator friction comprises:
from the hysteresis cycle data, determining said kinetic actuator friction by identifying a torque hysteresis value for at least one position value, wherein the kinetic actuator friction has a value that is half the value of the identified torque hysteresis.

8. A method according to claim 1, wherein the hysteresis cycle data are monitored under different thermal conditions, each thermal condition being represented by a temperature of at least one of the environment and a mechanical element of the joint, and the hysteresis cycle data being dependent on the temperature such that the determined properties vary with temperature, the method further comprising:
determining a dependency of the at least one joint property with respect to the temperature.

9. A method according to claim 1, wherein the method comprises actuating the at least one actuator via the drivetrain in order to determine joint property values for a first one of the individual joints (112, 114, 116-119, 180) in a clamping configuration with a second one of the individual joints, and repeating actuating the at least one actuator via the drive train in order to determine joint property values for the second one of the individual joints, where the clamping configuration of the first and second ones of the individual joints (112, 114, 116-119, 180) remains unchanged in the repetition of the actuating (210) and monitoring step.

10. A method according to claim 1, wherein said clamping step (a) comprises:
(a)(1) clamping at least a first joint (112, 114, 116-119, 180) in a first clamping configuration; and
(a)(2) clamping at least the first joint (112, 114, 116-119, 180) in a second clamping configuration different from the first clamping configuration; and
wherein the steps (b), (c), and (d) are performed for each of the first and second clamping configurations.

11. A method for determining at least one property of a joint (112, 114, 116-119, 180) of a manipulator (110), said method comprising positioning a movable part of said manipulator (110) at a clamping item (160) within a workspace of the manipulator (110) and contacting one point on the clamping item (160) with said movable part, and further comprising:
(a) clamping (200) said joint (112, 114, 116-119, 180) such that joint motion becomes constrained;
(b) actuating (210) said drivetrain with an actuator, while monitoring at least one quantity representing a torque of said actuator and at least one quantity representing the actuator position sensed with a motor angle sensor, such that the actuator reciprocates between a first position and a second position, and such that fully-developed drivetrain torque transmission, in opposite directions, is accomplished in both the first position and the second position, whereas the at least one monitored quantity representing the torque of said actuator and the at least one quantity representing the actuator position form hysteresis cycle data;
(c) determining (220) at least one set of output values of said actuator based on the obtained hysteresis cycle data, said set of output values being related to at least one joint position; and
(d) determining (230) the at least one property of the joint (112, 114, 116-119, 180) based on said at least one set of output values.

12. A method according to claim 11, further comprising:
obtaining nominal kinematic parameters for the manipulator (110); and
updating said nominal kinematic parameters based on said least one determined property of said joint (112, 114, 116-119, 180).

13. A method according to claim 11, wherein a drivetrain of a joint of the manipulator is actuated by the controller, said method further comprising updating the controller according to the determined at least one property of the joint of the manipulator.

14. A system (100) for determining at least one property of a joint (112, 114, 116-119, 180) of a manipulator (110), wherein the system includes at least one actuator configured to drive said joint (112, 114, 116-119, 180) via a drivetrain, the system (100) comprising:
a clamping device (160) configured to constrain joint motion of the joint (112, 114, 116-119, 180);
a controller (140) configured to control motion of said joint (112, 114, 116-119, 180) and to actuate said drivetrain such that the actuator reciprocates between a first position and a second position, and such that fully-developed drivetrain torque transmission, in opposite directions, is accomplished in both the first position and the second position;
means for monitoring at least one quantity representing a torque of said actuator and at least one quantity representing the actuator position sensed with a motor angle sensor, while actuating said drive train, wherein the at least one monitored quantity representing the torque of said actuator and the at least one quantity representing the actuator position form hysteresis cycle data;
means for determining at least one output value of said actuator based on the obtained hysteresis cycle data, said output value corresponding to at least one joint position; and
means for determining the at least one property of the joint (112, 114, 116-119, 180) based on said at least one output value.

15. A system (100) according to claim 14, further comprising a manipulator (110), wherein said joint (112, 114, 116-119, 180) is a part of the manipulator (110), wherein the controller (140) is configured to control the manipulator (110), and wherein the clamping device (160) is configured to enable docking and clamping of an end portion of the manipulator (110), such that the manipulator (110), when docked and clamped to the clamping device (160), attains a clamped pose.

16. A system (100) according to claim 14, wherein the clamping device (160) is configured to provide at least one point in space for clamping the manipulator (110) in order to determine at least one property of the joint of said manipulator (110).

17. A system (100) according to claim 14, wherein the controller comprises a digital computer programmed with a non-transitory computer-readable program that includes instructions to perform the steps of:
  controlling motion of said joint (112, 114, 116-119, 180) and actuating said drivetrain such that the actuator reciprocates between a first position and a second position;
  monitoring at least one quantity representing a torque of said actuator and at least one quantity representing the actuator position sensed with a motor angle sensor, while actuating said drive train, wherein the at least one monitored quantity representing the torque of said actuator and the at least one quantity representing the actuator position form hysteresis cycle data;
  determining at least one output value of said actuator based on the obtained hysteresis cycle data, said output value corresponding to at least one joint position; and
  determining the at least one property of the joint (112, 114, 116-119, 180) based on said at least one output value.

18. A computer readable medium having non-transiently stored thereon the computer program of claim 17.

* * * * *